United States Patent [19]
Collins et al.

[11] Patent Number: 6,136,223
[45] Date of Patent: *Oct. 24, 2000

[54] METAL LIGAND CONTAINING BLEACHING COMPOSITIONS

[75] Inventors: Terrence J. Collins; Colin P. Horwitz, both of Pittsburgh, Pa.

[73] Assignee: Carnegie Mellon University, Pittsburgh, Pa.

[ * ] Notice: This patent is subject to a terminal disclaimer.

[21] Appl. No.: 09/075,598

[22] Filed: May 11, 1998

Related U.S. Application Data

[63] Continuation-in-part of application No. 08/804,776, Feb. 24, 1997, Pat. No. 5,853,428, which is a continuation-in-part of application No. 08/684,670, Jul. 22, 1996, Pat. No. 5,876,625.

[51] Int. Cl.[7] .................... C01B 15/00; C01B 15/055; C11D 3/39
[52] U.S. Cl. .................... 252/186.33; 252/186.43; 252/186.39; 510/311; 540/460; 540/465
[58] Field of Search .................... 252/186.33, 186.43, 252/186.39; 162/74, 79, 4, 5, 6, 70; 8/107, 108.1, 111; 540/460, 452, 465; 510/311

[56] References Cited

U.S. PATENT DOCUMENTS

| | | | |
|---|---|---|---|
| 3,736,224 | 5/1973 | Grayson et al. | 162/65 |
| 4,590,005 | 5/1986 | Shanzer et al. | 549/11 |

(List continued on next page.)

FOREIGN PATENT DOCUMENTS 0 458 398 A2  11/1991  European Pat. Off. .

OTHER PUBLICATIONS

Terrence J. Collins, Designing Ligands For Oxidizing Complexes, Dept. Of Chem. Carnegie Mellon University, Accounts Of Chemical Reseach, (1994) 27, p. 279.

(List continued on next page.)

*Primary Examiner*—Joseph D. Anthony
*Attorney, Agent, or Firm*—Kirkpatrick & Lockhart LLP

[57] ABSTRACT

The invention provides a novel composition and method for removing or reducing levels of recalcitrant constituents from an effluent, such as lignin chromophores, AOX species, such as chlorinated phenols, dioxins, dibenzofurans, biphenyls, and high molecular weight material produced in the pulp and paper bleaching operations which includes using a composition comprised of (a) an amount of a source of an oxidant effective for oxidizing and thereby reducing the levels of such constituents and (b) an oxidatively stable oxidant activator having the structure

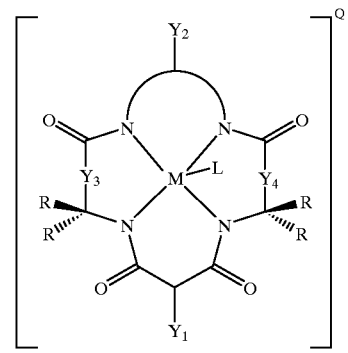

wherein $Y_1$, $Y_3$ and $Y_4$ each represent a bridging group having zero, one, two or three carbon containing nodes for substitution, and $Y_2$ is a bridging group having at least one carbon containing node for substitution, each said node containing a C(R), $C(R_1)(R_2)$, or a $C(R)_2$ unit and each R substituent is the same or different from the remaining R substituents; M is a transition metal with oxidation states of I, II, III, IV, V, VI, VII or VIII or selected from Groups 3, 4, 5, 6, 7, 8, 9, 10 and 11 of the Periodic Table of the Elements; and Q is any counterion which would balance the charge of the compound on a stoichiometric basis.

13 Claims, 10 Drawing Sheets

U.S. PATENT DOCUMENTS

| | | | |
|---|---|---|---|
| 4,773,966 | 9/1988 | Huynh | 162/78 |
| 5,032,286 | 7/1991 | Newman et al. | 210/737 |
| 5,244,594 | 9/1993 | Favre et al. | 252/186.33 |
| 5,246,621 | 9/1993 | Favre et al. | 252/186.33 |
| 5,288,746 | 2/1994 | Pramod | 435/189 |
| 5,314,635 | 5/1994 | Hage et al. | 252/186.33 |
| 5,580,485 | 12/1996 | Feringar et al. | 510/311 |

OTHER PUBLICATIONS

Erich Stuart Uffelman, Macrocyclic Tetraamido–N–Ligands That Stabilize High Valent Complexes Of Chrominum, Maganese, Iron, Colbalt, Nickel, and Copper, California Institute Of Technology, (Aug. 19, 1991).

Kimberely K. Kostka, Synthesis And Characterization Of high–Valent, Iron Complexes Of Macrocyclic Tetraamido–N–Ligands, Carnegie Mellon University, (Jul. 19, 1993).

Reaction conditions:
Catalyst: [Fe(DCB*) (H2O)]⁻
Oxidant: 5000 equiv. H₂O₂
T: 25° C
pH: 10(0.1 M Na₂CO₃/NaHCO₃)
Sequesterant: Dequest 2066

∗ = add 60 µL of saturated solution of alkali lignin and H₂O₂ (5000 equiv)

Catalyst:
0.4 mM [Fe(H2O)DCB*]$^-$
0.4 mM [Fe(H2O)DCB]$^-$
0.0 mM catalyst
12 μM pinacyanol chloride dye
4 mM 30% H2O2 oxidant
pH ~ 9 NaHCO3/Na2CO3

* = dye addition    time / s

METAL LIGAND CONTAINING BLEACHING COMPOSITIONS

CROSS REFERENCE TO RELATED APPLICATION

This is a continuation in part of U.S. patent application Ser. No. 08/804,776, filed Feb. 24, 1997 now U.S. Pat. No. 5,853,428, which is a continuation in part of U.S. patent application Ser. No. 08/684,670, filed Jul. 22, 1996 now U.S Pat. No. 5,876,625.

STATEMENT REGARDING FEDERALLY SPONSORED RESEARCH

This work was supported by the National Science Foundation, grant CHE9319505, and the National Institute of Health, grant GM-44867. The United States government may have certain rights in this application.

BACKGROUND OF THE INVENTION

The invention relates to the use of macrocyclic metal-ligand complexes as bleaching catalysts, and more particularly, to transition metal complexes of macrocyclic tetraamide ligands as catalysts for enhancing oxidative bleaching reactions.

The United States and Canada are the world's leading producers of wood pulp used for the production of paper and paper board. In 1994, the United States produced over 58 million tons of wood pulp. Pulp, which is made either mechanically or chemically from wood, contains 1) cellulose, a homopolysaccharide linear polymer of d-glucose of the formula —$(C_6H_{10}O_5)$—; 2) lignin, a non-uniform three dimensional molecule having the following general composition, $C_9H_{8.83}$ $O_{2.37}$ $(OCH_3)_{0.96}$; and 3) hemicellulose, a heteropolysaccharide polymer. See generally, W. G. Glasser and S. Sarkanen, eds. "LIGNIN PROPERTIES AND MATERIALS," American Chemical Society Symposium, Series 397.

Desirable qualities for paper include strength, whiteness and brightness. The strength of the paper is related to the viscosity of the pulp employed in its manufacture which, in turn, is related to the condition of the cellulose after the pulping operation. Molecular cellulose, as explained above, is a linear chain of d-glucose which naturally forms long fibers. The longer the individual cellulose polymer chains, the higher the viscosity of the pulp, and in turn, the greater the strength of the paper. Thus, during processing, it is most desirable to avoid cleaving the cellulose polymers into smaller units.

Whiteness is based on the appearance of the paper to observers and its measure is therefore subjective. Brightness is a term used to describe the whiteness of pulp on a scale from 0% (absolute black) to 100% (relative to a MgO standard, which has an absolute brightness of ca. 96%) by the reflectance of blue light (457 nm) from the paper produced from the pulp. The more incident light that is reflected, rather than absorbed, the brighter the paper.

Brightness is obtained by bleaching. Pulp bleaching is defined as the treatment of cellulose fibers with chemicals to increase brightness. Bleaching chemicals increase brightness by removing and decolorizing the lignin in the pulp. Lignin exhibits a yellowish to a deep brown color, depending on the type of wood.

The most common bleaching chemicals are the oxidants chlorine, a source of hypochlorite ion, and chlorine dioxide. Oxygen gas in conjunction with NaOH may also be used, but requires expensive equipment and must be used in large amounts. Oxygen also results in loss of pulp strength resulting from free radical damage to the cellulose polymers, particularly when the lignin content of the pulp is low.

Chlorine and hypochlorite can result in loss of strength if used improperly, but in general are effective and relatively easy to use oxidants. Hypochlorite is an aggressive oxidant that is prone to attacking the cellulose, especially if nonoptimally employed. Chlorine dioxide achieves a high level of brightness without pulp degradation. However, it is an expensive oxidant and it is prone to explosive decomposition. All the chlorine based oxidants produce as effluent chlorinated byproducts that are hazardous to the environment and to health. Moreover, effluent that contains chlorine in any chemical form cannot be burned in the recovery boiler of a pulp mill. The chlorine produces corrosion of the recovery boiler. Moreover, as noted below, combustion of chlorine containing species can lead to the production of polychlorinated dioxins and dibenzofurans, 17 of which are considered toxic and carcinogenic. In addition, chlorine, for example, can react violently with combustible materials. It reacts with $H_2S$, CO and $SO_2$ to form toxic and corrosive gases; and, in liquid form, causes burns, blistering and tissue destruction. In gaseous form, it causes severe irritation to eyes, nasal passages and respiratory tissue. In high doses, it can be lethal. Chlorine dioxide bleach decomposes into $Cl_2$ which is toxic and corrosive.

Polychlorinated aromatic compounds are environmental pollutants. The most well known examples are DDT, the polychlorinated phenols, dioxins, dibenzofurns and polychlorinated biphenyls (PCBs). These types of compounds can be formed when appropriate organic compounds are exposed to chlorine containing oxidants. The combustion of organic matter in the presence of chlorine in any form can produce dioxin. Even though dioxins and PCBs are no longer manufactured, there are chemical processes that form these compounds from polychlorinated phenol precursors. There is a need to prevent the unwanted formation of polychlorinated aromatic compounds and to remediate those that are present in the environment.

In the pulp and paper industry, chlorinated organics (monochlorinated and polychlorinated), collectively called "absorbable or adsorbable organic halogen" or "AOX", are formed upon bleaching of wood pulp with chlorine based oxidants. One such compound is 2,4,6-trichlorophenol, TCP, which is produced, for example, during the bleaching process when chlorine is used as the bleaching agent. TCP ends up in the waste stream leaving the plant.

Notwithstanding the hazards to the environment, the chlorine-based oxidants are the most widely used for pulp bleaching in the United States. Commercial pulp and paper bleaching facilities actually use a combination of several methods. One widely used bleaching sequence begins with chlorination, followed by extraction with NaOH, treatment with chlorine dioxide, more NaOH extraction and then more chlorine dioxide treatment. A modification of that sequence adds a hypochlorite oxidation step between the first NaOH extraction and first treatment with chlorine dioxide. In another sequence, the second NaOH extraction and second chlorine dioxide treatment are eliminated.

On Nov. 14, 1997, the United States Environmental Protection Agency signed a Cluster Rule requiring the Pulp and Paper Industry to reduce chlorinated organics production. To meet the effluent reduction requirements, the industry is primarily expanding the use of what is called "elemental chlorine free" (ECF), which is a term used primarily for bleaching with chlorine dioxide. The important point is that chlorine dioxide bleaching produces considerably less toxic effluent than does bleaching with elemental chlorine, $Cl_2$. Nevertheless, some AOX is produced and a further disadvantage is that the bleach plant effluent cannot be burned in the recovery boiler as noted above. In addition, the industry has been developing what is calls "totally chlorine free" (TCF) bleaching. The principal oxidants of TCF bleaching are oxygen and hydrogen peroxide, although ozone also has a position. Hydrogen peroxide oxidizes and brightens lignin and produces high yields of pulp. It is easier to use than oxygen and it does not require expensive equipment, one of the big disadvantages of oxygen bleaching. In use, it is generally believed that $H_2O_2$ dissociates to produce the perhydroxyl ion, OOH—, which decolorizes lignin and does not attack cellulose. However, if $H_2O_2$ decomposes, it produces free radicals which fragment the lignin as desired, but also degrades the cellulose. The principal offending radical is the hydroxyl radical, HO• which is notoriously nonselective. Because the H—O bond of water is so strong (ca. 119 kcal.morl$^{-1}$), the HO• radical will abstract H atoms rapidly from a wide variety of organic compounds and, indeed, from most H-atom sources. For this reason, pulp is generally treated with a sequestering agent prior to peroxide treatment. The purpose of the sequestering agent is to remove metal ions which decompose the peroxy compound producing radicals. Furthermore, peroxide bleaching methods will often include the addition of further sequestering agent, again for shielding the peroxy compound from exposure to trace amounts of metal which can decompose it unnecessarily and lower its selectivity. While hydrogen peroxide itself is a strong oxidant which can burn skin and mucous membranes, it is not a serious hazard in low (<8%) concentrations. Most importantly, its use does not introduce elemental toxicity into the environment. Peroxide is an excellent brightening agent. The major drawback to use of $H_2O_2$ as the oxidant for pulp and paper bleaching is that it is not as selective at delignifying pulp as chlorine dioxide. The process proceeds relatively slowly such that the pulp and peroxide must be heated. Historically, peroxide was a comparatively expensive oxidant. However, peroxide prices have been falling and mills have the option for onsite generation. Although $H_2O_2$ would clearly be preferred for its environmentally friendly characteristics, the selectivity factors and operating costs associated with its use have contributed to reducing its commercial desirability. When used commercially, it has been primarily as a brightening agent for mechanical pulp used, for example, in newsprint when long term stability of the color is not needed and the lignin is primarily decolorized rather than being essentially removed, or as an adjunct to chlorination and/or chlorine dioxide bleaching and/or oxygen bleaching or to oxidize the effluent.

The environmental impacts of wastewaters produced by pulp and paper processing have been the focus of significant research over the past 30 years. The traditional areas of concern have been oxygen demand, suspended solids and acute toxicity. Improvements in control strategies within mills, pulping and bleaching technology, and secondary treatment systems have addressed these issues to a large extent. There is now an increasing focus on potential subacute toxicity (e.g. reproductive effects), residual nutrients/eutrophication, and recalcitrant constituents, especially color and organochlorine. Reductions in wastewater color and absorbable organic halogen mass loadings following biological treatment may average 10% and 40%, respectively. In some cases, significant increases in color levels may occur. Approximately 50% of the soluble chemical oxygen demand in bleached kraft mill effluents (BKME) also remains following secondary treatment and appears to consist of recalcitrant high molecular mass material (HMM). The higher molecular mass constituents (MW>1000 Daltons) in BKME consist primarily of highly degraded, chlorinated lignin degradation products with some residual polysaccharide constituents. In BKME, this material may constitute 40–90% of the total organic material, approximately 80% of the AOX content, and 60–100% of the color loadings from the mill. Little information is available on the chemical nature or mass flows of color and HMM discharged from other mill operations (e.g. mechanical pulping).

Scandinavian and North American studies have shown that these recalitrant chromophoric, halogenated and carbonaceous constituents are highly persistent in freshwater systems and may be detected hundreds of kilometers from the discharge source. The colored material has obvious effects on the aesthetics of receiving water as well as decreasing photic depth in the water column and thus the available habitat for macrophytes, and planktonic and benthic food sources. HMM was previously considered to be nonbioaccumulative, non-toxic and inert because of its large molecular size and water solubility. More recent studies now indicate that bioaccumulation of some of this material-can occur in exposed organisms and HMM has been implicated as the major toxicant inhibiting fertilization capacity in some marine species (e.g. echinoderms). HMM may also absorb low molecular weight lipophilic ecotoxicants such as chlorophenolics. This association may significantly effect the dispersal and transportation of these ecotoxicants and alter their bioavailability to recipient organisms.

Given these concerns, the pulp and paper industry is under considerable pressure to effectively remove these wastewater constituents. A large number of advanced technologies exist, in various stages of development, that have potential application for their environmental control. These include ultrafiltration; flocculation; electrotechnologies such as ozonolysis, photolysis, and wet oxidation; and incineration and plasmolysis. Significant potential exists for the application of a number of different technologies to give the desired treatment, such as the use of advanced treatment in conjunction with biological and/or membrane separation technology.

Advanced oxidative technologies, for example using ozone or peroxide, have shown particular promise as highly effective means of removing organochlorine or color from pulp and paper wastewaters. However, the high levels of peroxide required in treatments developed to date would appear to make this technology as prohibitively expensive as the other methods.

Certain transition metal chelates have been researched for unrelated purposes. For example, complexes of high oxidation state transition metals are known to function as oxidants in numerous biological reactions under the influence of a protein matrix and in recent years a widespread interest in understanding the mechanism of action and the reactivity of certain monooxygenase catalysts has developed.

An exemplary program is described in Collins, T. J., "Designing Ligands for Oxidizing Complexes," *Accounts of Chemical Research*, 279, Vol. 27, No. 9 (1994). This article lays out a design oriented approach for obtaining ligands that are resistant to oxidative degradation when coordinated to highly oxidizing metal centers. Several diamido-N-diphenoxido and diamido-N-alkoxido acyclic chelate compounds and macrocyclic tetraamido-N chelate compounds are described in the Collins Accounts of Chemical Research article.

An azide based synthetic route to macrocyclic tetraamido metal ligand complexes is described in Uffelman, E. S., Ph.D. Thesis, California Institute of Technology, (1992). Additionally, synthesis of an aryl bridged tetraamido ligand via the azide based route can proceed by using an aromatic diamine as a starting material.

However, the art has not recognized that certain macrocyclic tetraamido metal ligand complexes will provide novel and unusually effective bleach activators for peroxy compounds. Additionally, it has not been taught, disclosed or suggested that these types of compounds will be unusually advantageous in the areas of pulp and paper bleaching.

SUMMARY OF THE INVENTION

The invention comprises a composition comprising:

(a) an oxidatively stable oxidant activator having the structure

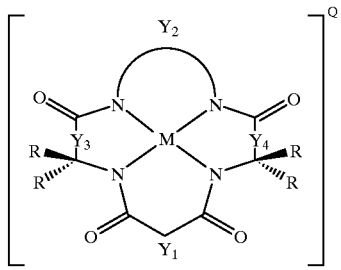

wherein $Y_1$, $Y_3$ and $Y_4$ each represents a bridging group, having zero, one, two or three carbon containing nodes for substitution, and $Y_2$ is a bridging group having at least one carbon containing node for substitution, each said node containing a $C(R)$, $C(R_1)(R_2)$, or a $C(R)_2$ unit and each R substituent is the same or different from the remaining R substituents and (i) is selected from the group consisting of alkyl, cycloalkyl, cycloalkenyl, alkenyl, aryl, alkynyl, alkylaryl, halogen, alkoxy, or phenoxy, $CH_2CF_3$, $CF_3$ and combinations thereof, or (ii) form a substituted or unsubstituted benzene ring of which two carbon atoms in the ring form nodes in the Y unit, or (iii) together with a paired R substituent bound to the same carbon atom form a cycloalkyl or a cycloalkenyl ring, which may include an atom other than carbon, e.g., cyclopropyl, cyclobutyl, cyclopentyl, or a cyclohexyl ring; M is a transition metal with oxidation states of I, II, III, IV, V, VI, VII or VIII or selected from Groups 3, 4, 5, 6, 7, 8, 9, 10, 11 and 12 of the Periodic Table of the Elements; Q is any counterion which would balance the charge of the compound on a stoichiometric basis; and (b) an amount of a source of an oxidant effective for oxidizing a target, such as the byproducts of the pulp and paper bleaching process. The oxidation may be for the purpose of bleaching a substrate, such as a fabric or wood pulp or paper and other cellulosic materials, oxidizing lignin, bleaching lignin, delignifying pulp, decolorizing chromophores, such as lignin chromophores or lignin-derived chromophores, or for oxidizing adsorbable or absorbable organic halogens and recalcitrant carbonaceous constituents in the effluent of an industrial operation, such as a pulp and paper processing operation. The byproducts of the pulp and paper making process also include the absorbable organic halogen species, such as aromatic compounds. Aromatic compounds include chlorinated phenols, dioxins, dibenzofurans, biphenyls and combinations thereof Sequesterants, stabilizers and other standard pulp and paper bleaching adjuncts well known to those skilled in the art of pulp and paper bleaching may be added.

The preferred oxidant activators are macrocyclic tetraamido metal ligand complexes. Of these, those having a substituted aromatic substituent fused directly into the ligand's cyclic structure are especially preferred.

For example, a preferred compound has the structure:

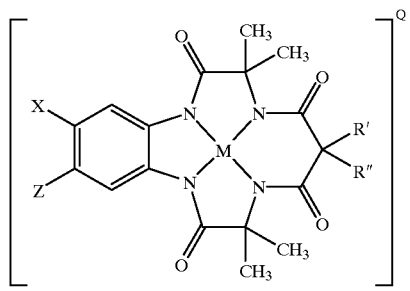

wherein X and Z may be H, electron-donating or electron-withdrawing groups and R' and R" may be any combination of H, alkyl cycloalkyl, cycloalkenyl, alkenyl, aryl, alkynyl, alkylaryl, halogen, alkoxy, or phenoxy substituents, or combine to form a cycloalkyl or cycloalkenyl ring, which may contain at least one atom that is not carbon; M is a transition metal with oxidation states of I, II, III, IV, V, VI, VII or VIII or selected from Groups 3, 4, 5, 6, 7, 8, 9, 10, 11 and 12 of the Periodic Table of the Elements; Q is any counterion which would balance the charge of the compound on a stoichiometric basis.

The rapid growth in the pulp and paper industry and the increasing reliance on chemical bleaching processes to provide bright, strong paper products necessarily causes the release of chlorinated byproducts into the environment. The industry needs a safer alternative to chlorine based oxidants for bleaching. Any such bleaching technology will be all the more desirable if it effects the bleaching of colored effluents from any process in the mill. The desirability will also be enhanced if the oxidizing system can attack and decompose HMM, AOX and BKME as well as effluents from any other type of mill.

The compounds of the present invention significantly improve the performance of peroxide for pulp bleaching applications with substantial reductions in chemical requirements. The compound and oxidant composition may be used for the treatment of color, organochlorine and recalcitrant carbonaceous materials in pulp.

There is a need for a method for bleaching pulp which significantly reduces the discharge of toxic substances into the environment either in the preparation of pulp or in the treatment of effluent or both. There is a further need for an environmentally nontoxic method which is easy to use and which will produce bright, strong paper.

The compound of the present invention has been determined to be particularly well-suited to handle these tasks. The compound has been shown to rapidly increase the rate of lignin bleaching upon the addition of hydrogen peroxide. Furthermore, the compound of the present invention has been shown to be very stable under catalytic oxidation conditions including the bleaching of pulp or the oxidation of effluents.

There is a need for a novel oxidant activator which has sustained catalytic stability in a buffered solution.

There is a further need for a novel oxidant activator which can be used in substoichiometric amounts relative to the oxidant compound.

The present invention provides a method for the oxidative degradation of polychlorinated phenols and for the decolorization of chromophores in pulp and paper wastewaters. The method comprises generally, the steps of contacting the effluent with a source of an oxidant, preferably a peroxy compound, and more preferably hydrogen peroxide and/or its dissociation products, and catalytic, or substoichiometric, amounts of the activator of the composition described above. The method may further include the addition of a sequesterant for shielding the peroxy compound from exposure to trace amounts of metal ions which can decompose it unnecessarily.

The method may be run at a variety of temperatures, but preferably within the range of ambient to about 130° C., and more preferably between ambient to 90° C. Ranges of ambient to about 40° C. may also be successfully used. Temperature, however, does not appear to be critical. A wide range of temperatures are suitable. Those skilled in the art will recognize that the pressure of the system would have to be increased at higher temperatures.

The preferred pH range is between 7 and 12, and preferably between 9 and 11.

While the activator of the present invention has been shown in other applications to be an excellent activator for oxidation reactions in solution in general, and particularly as an activator for activating O-atom transfer oxidants, such as hydrogen peroxide, t-butyl hydroperoxide, cumyl hydroperoxide, hypochlorite and peracids, the preferred use in the method of the present invention is as an activator of peroxy compounds, and most preferably as an activator of hydrogen peroxide, with or without oxygen, in pulp and paper bleaching. The composition of the present invention enhances the oxidative capabilities of hydrogen peroxide, thereby greatly enhancing the commercial utility of this environmentally friendly oxidant.

Thousands upon thousands of metric tons of environmentally undesirable and even highly toxic, mutagenic or carcinogenic byproducts no longer need to be generated. The method of the present invention can significantly reduce, if not replace the use of chlorine-based bleaching oxidants and the toxic byproducts their use generates. The method of the present invention can be used to treat kraft pulp in an early bleaching step to be followed by the use of chlorine dioxide for further bleaching and brightening, and/or by uncatalyzed peroxide for further bleaching and brightening. It is reasonable to expect that the method of the present invention can also be used to enhance oxygen treatment of pulp by the addition of the activator and peroxide to oxygen bleaching cycles. It is further reasonable to expect that the method of the present invention can be used to brighten pulp at or near the end of a multiple treatment bleaching sequence.

DETAILED DESCRIPTION OF THE PREFERRED EMBODIMENTS

The invention comprises a composition comprising:

(a) an oxidatively stable activator having the structure

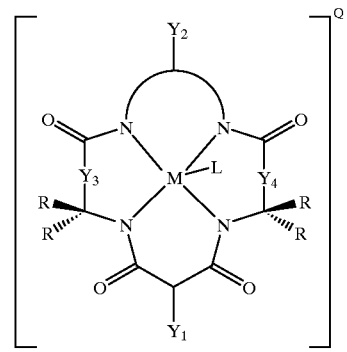

wherein $Y_1$, $Y_3$ and $Y_4$ each represents a bridging group having zero, one, two or three carbon containing nodes for substitution, and $Y_2$ is a bridging group having at least one carbon containing node for substitution, each said node containing a C(R), C($R_1$)($R_2$), or a C(R)$_2$ unit and each R substituent is the same or different from the remaining R substituents and is selected from the group consisting of H, alkyl cycloalkyl, cycloalkenyl, alkenyl, aryl, alkynyl, alkylaryl, halogen, alkoxy, or phenoxy, $CH_2CF_3$, $CF_3$ and combinations thereof, or form a substituted or unsubstituted benzene ring of which two carbon atoms in the ring form nodes in the Y unit, or together with a paired R substituent bound to the same carbon atom form a cycloalkyl or cycloalkenyl ring, which may include an atom other than carbon, e.g., cyclopropyl, cyclobutyl, cyclopentyl or a cyclohexyl ring; M is a transition metal with oxidation states of I, II, III, IV, V, VI, VII or VIII or selected from Groups 3, 4, 5, 6, 7, 8, 9, 10, 11 and 12 of the Periodic Table of the Elements; Q is any counterion which would balance the charge of the compound on a stoichiometric basis; and L is optionally present and may be any labile ligand; and (b) an amount of a source of an oxidant effective for oxidizing a target. The oxidation may be for the purpose of bleaching a substrate, such as a fabric or wood pulp or paper and other cellulosic materials, oxidizing lignin, bleaching lignin, delignifying pulp, decolorizing chromophores, such as lignin chromophores, or for oxidizing adsorbable organic halogen (AOX) and recalcitrant carbonaceous constituents in the effluent of an industrial operation, such as a pulp and paper processing operation.

Of these, the preferred inventive macrocyclic tetraamido metal ligand complexes have proven to be surprisingly effective in a diverse group of performance characteristics for oxidant activators.

Figure 3:
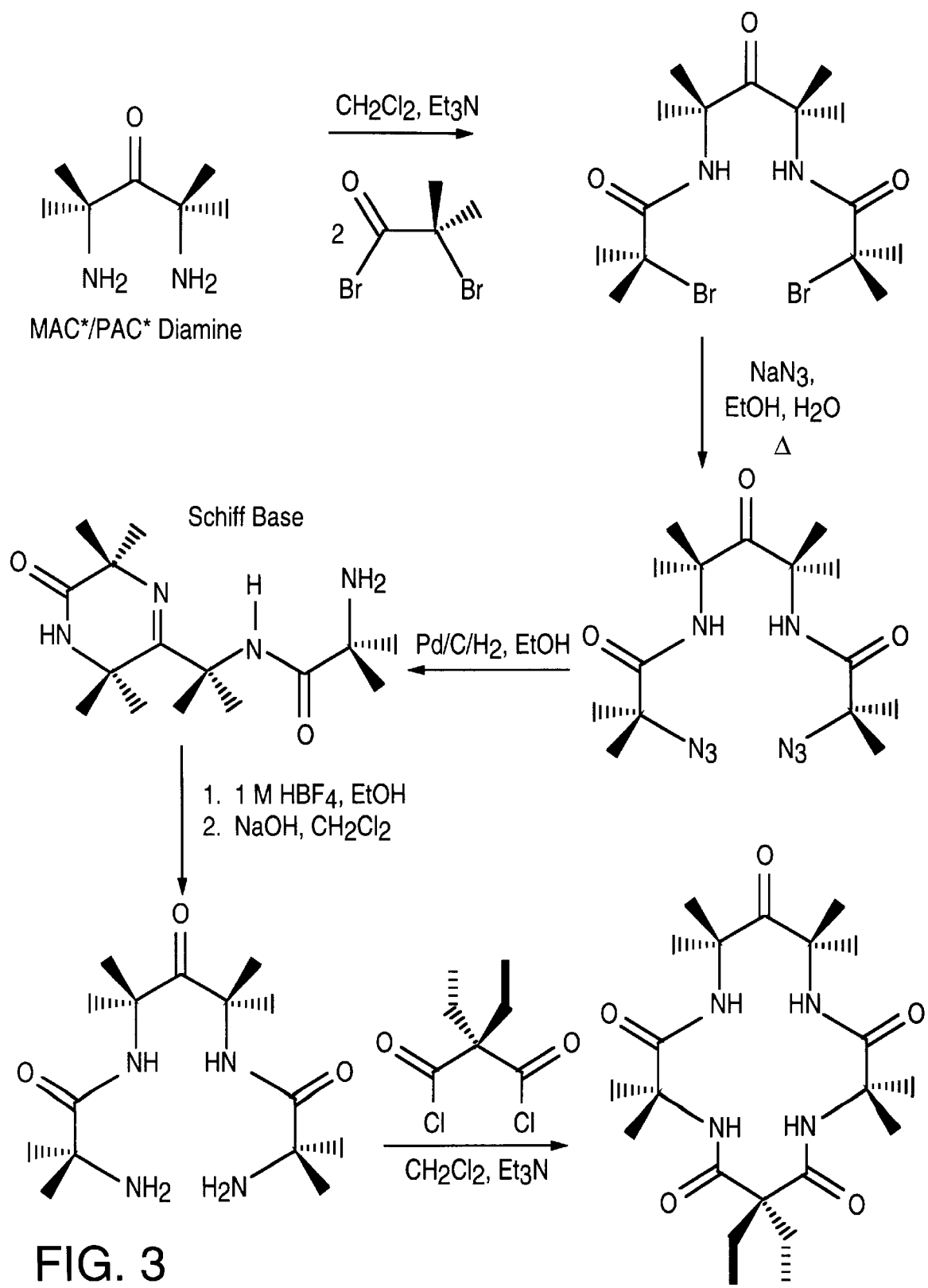
FIG. 3 depicts a synthetic route for preparing the macrocyclic tetraamido metal ligand complexes of the invention via the azide route.
Figure 4:
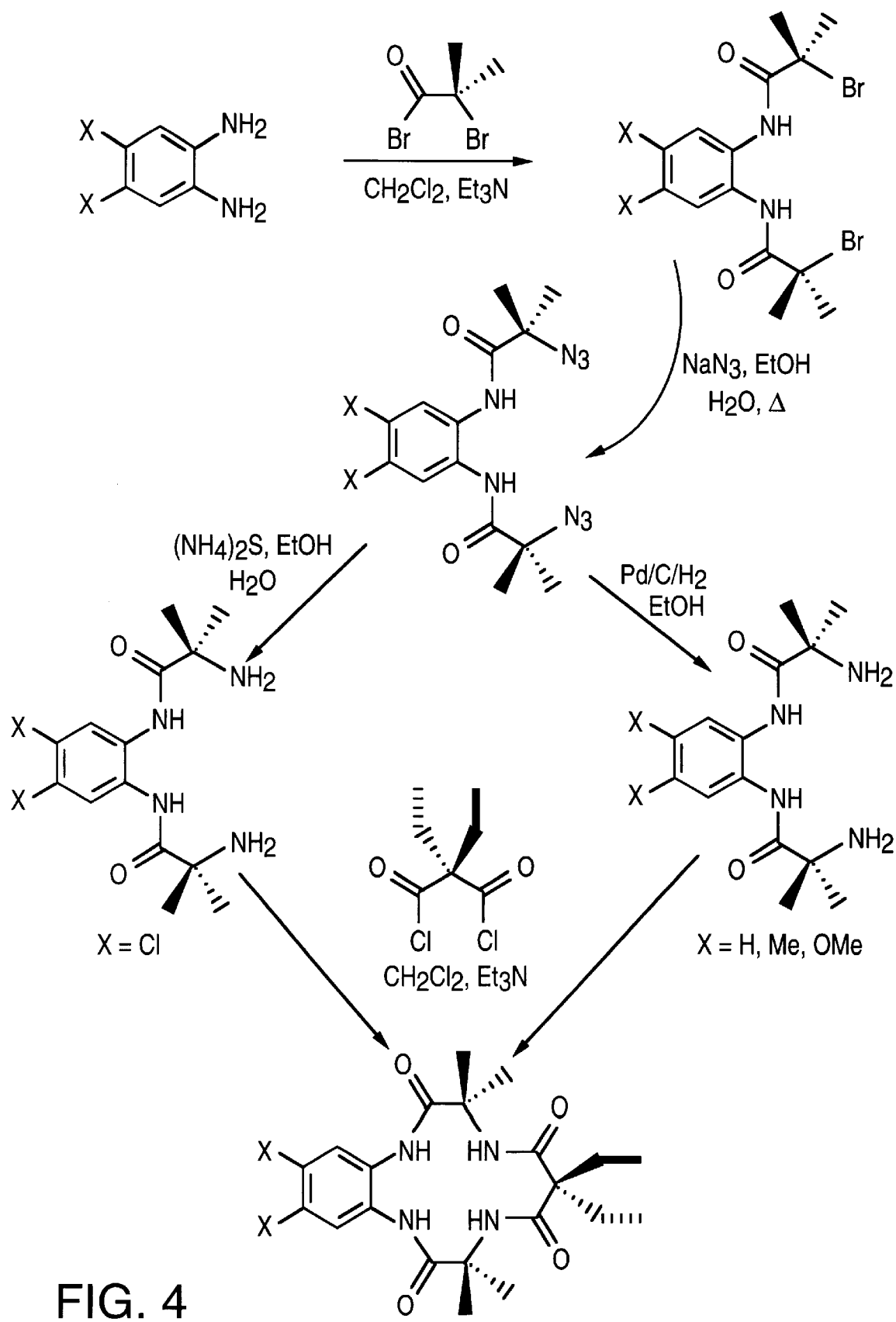
FIG. 4 depicts a synthetic route for preparing the macrocyclic tetraamido metal ligand complexes of the invention via the azide route using an aromatic diamine as a starting material.

These ligands are prepared in accordance with the procedures shown in FIGS. 3 or 4, and set forth in the co-pending patent application of Gordon-Wylie et al., entitled SYNTHESIS OF MACROCYCLIC TETRAAMIDO-N LIGANDS, Ser. No. 08/681,187, filed Jul. 22, 1996, which is incorporated herein by reference, and include, in addition to the compounds described herein, the ligands set forth in detail in co-pending patent application of Collins et al., entitled LONG-LIVED HOMOGENEOUS OXIDATION CATALYSTS, Ser. No. 08/681,237, filed Jul. 22, 1996, which is incorporated herein by reference.

1. The Macrocyclic Tetraamido Metal Ligand Complexes

The inventive compounds have the structure:

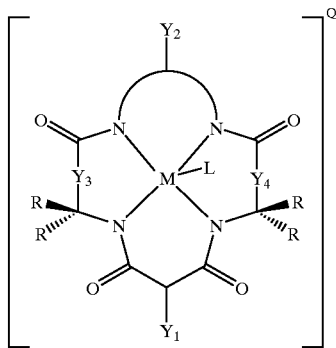

wherein $Y_1$, $Y_3$ and $Y_4$ each represents a bridging group having zero, one, two or three carbon containing nodes for substitution, and $Y_2$ is a bridging group of at least one carbon containing node for substitution, each said node containing a C(R), C($R_1$)($R_2$), or a C(R)$_2$ unit and each R substituent is the same or different from the remaining R substituents and is selected from the group consisting of alkyl, cycloalkyl, cycloalkenyl, alkenyl, aryl, alkynyl, alkylaryl, halogen, alkoxy, orphenoxy, $CH_2CF_3$, $CF_3$ and combinations thereof, or form a substituted or unsubstituted benzene ring of which two carbon atoms in the ring form nodes in the Y unit, or together with a paired R substituent bound to the same carbon atom form a cycloalkyl or cycloalkenyl ring, which may include an atom other than carbon, e.g., cyclopropyl, cyclobutyl, cyclopentyl or cyclohexyl ring; M is a transition metal with oxidation states of I, II, III, IV, V, VI, VII or VIII or selected from Groups 3, 4, 5, 6, 7, 8, 9, 10, 11 and 12 of the Periodic Table of the Elements; Q is any counterion which would balance the charge of the compound on a stoichiometric basis; L is optionally present and may be any labile ligand.

An especially preferred embodiment of these inventive compounds is represented by the structure of the macrocyclic tetraamido metal ligand complex

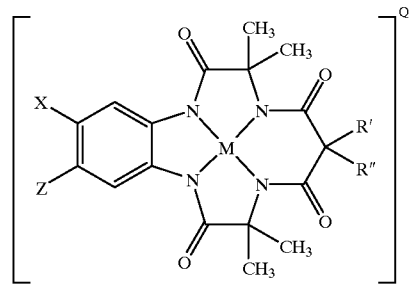

wherein X and Z may be H, electron donating or electron-withdrawing groups and R' and R" may be any combination of H, alkyl, cycloalkyl, cycloalkenyl, alkenyl, aryl, alkynyl, alkylaryl, halogen, alkoxy, or phenoxy substituents, or combine to form a cycloalkyl or cycloalkenyl ring, which may contain at least one atom that is not carbon: M is a transition metal with oxidation states of I, II, III, IV, V, VI, VII or VIII or selected from Groups 3, 4, 5, 6, 7, 8, 9, 10, 11 and 12 of the Periodic Table of the Elements; Q is any counterion which would balance the charge of the compound on a stoichiometric basis. L is optionally present and may be any labile ligand.

The X and Z groups can be H, or either electron donors or electron withdrawing groups. Electron withdrawing groups include halogens, such as Br, I and most preferably, $Cl^-$. Further, $SO^-_3$, $OSO_3^-$, $OSO_3R$ (R being defined, without limitation, as H, alkyl, aryl, alkylaryl) and $NO^-_2$ are appropriate groups. Electron donor groups include alkoxy (without limitation, methoxy, ethoxy, propoxy and butoxy), alkyl (without limitation, methyl, ethyl, propyl, n-butyl and t-butyl) and hydrogen. These groups change the electron density of the metal ligand complex and impact its reactivity.

R' and R" appear to have an impact on the sustained catalytic stability of the inventive macrocyclic tetraamido ligands. Although each can be individually chosen from H, alkyl, alkenyl, aryl, alkynyl, halogen, alkoxy, or phenoxy substituents, short chain alkyl appears preferred. Especially preferred is when R' and R" are the same and are selected from ethyl and methyl, or when R' and R" combine to form a cycloalkyl or cycloalkenyl ring, especially cyclopropyl, cyclobutyl, cyclopentyl or cyclohexyl. The cycloalkyl ring may include at least one other atom other than carbon, such as, without limitation, N, O, or S. The most preferred and most robust embodiments are those in which R' and R" are the same and are selected from the group consisting of methyl, $CF_3$, hydrogen, halogen and a four membered ring formed together with the carbon atom to which both are bound. These latter groups are either unreactive, form strong bonds with the cyclic carbon, are sterically hindered, and/or are conformationally hindered such that intramolecular oxidative degradation is restricted.

The tetradentate macrocyclic compound of the present invention is designed to be complexed with a metal, preferably a transition metal. The metal M is a transition metal with oxidation states of I, II, III, IV, V, VI, VII or VIII; or may be selected from Group 3 (Sc, Y, lanthanides and Actinides), Group 4, (Ti, Zr, Hf), Group 5 (V, Nb, Ta), Group 6 (Cr, Mo, W), Group 7 (Mn, Tc, Re), Group 8 (Fe, Ru, Os), Group 9 (Co, Rh, Ir), Group 10 (Ni, Pd, Pt) and Group 11 (Cu, Ag, Au). It is preferably selected from the group consisting of Sc, Ti, V, Cr, Mn, Fe, Co, Ni, Cu, Zn (Group 12), Mo and W.

Q is any counterion which would balance the charge of the compound on a stoichiometric basis. Both negative and positive counterions may be useful. A generally positively charged counterion is preferably chosen from, but not limited to: alkali metal counterions (e.g., K, Li, Na), $[NR^*_4]^+$ and $[PR^*_4]^+$, wherein each R* is individually selected from H, alkyl, aryl, alkylaryl, alkenyl, or can fuse together to form a cycloalkyl or cycloalkenyl or aryl ring which may contain at least one atom other than carbon. A generally negatively charged counterion is preferably chosen from, but not limited to $[BF_4]^{-1}$ and $[PF_6]^{-1}$.

L is any labile ligand which can attach to M. These include, preferably, but without limitations, $H_2O$, $Cl^-$, and $CN^-$.

Because of the complex nature of these compounds, within the specification, they are not named, but for convenience are referred to by the substituents present in them. The structure represented above, for example, can be titled 5,6(4,5-Di-X-Benzo)-3,8,11,13-tetraoxo-2,2,9,9-tetramethyl-12,12-diethyl-1,4,7,10-tetraazacyclotridecane (or Tetramethyl diethyl di-X-benzene (TMDE-DXB, where X=Cl, H, Me, OMe)). Thus, for convenience, in the above structure, where there are two methyl groups each on the carbon ax to an amide donor of the ligand, and there are two ethyl groups acting as R' and R", the compound is referred to as TMDE-DXB. When R' and R" are methyl groups, the compound is referred to as TMDM-DXB. When the groups X and Z are both chloro, the compound is referred to as TMDE-DCB or TMDM-DCB. A further shortening of the name of the compounds is used throughout where for example TMDE-DCB is referred to as DCB and TMDM-DCB is referred to as DCB*, the * specifically denoting that R' and R" are methyl. The preferred transition metal of the ligand is iron, so the compound with Fe(III) and the axial ligand $H_2O$ can be referred to as $[Fe(H_2O)DCB]^-$.

The conventional hydrogen peroxide bleaching methods are practiced at a pH within the range of 11 to 9 and at temperatures within the range of 30 to 80° C., and most often at 50 to 70°. See, Charles, J. E. et al., 1980 TAPPI Pulping Conference Proceedings, TAPPI Press (1980). When one of the activators of the present invention is used, the temperature of the reaction can be reduced to ambient temperature. While the catalyst activators can be used at the higher conventional reaction temperatures, they also works well at 35 and 40° C. In some applications, a higher temperature may be preferred, for example, a temperature up to about 130° C., and preferable within a range of ambient to 90° C. It is known that, for about every ten degrees in temperature, the reaction rate changes by a factor of about two. Thus, the reaction rate is much faster at higher temperatures. However, when bleaching pulp with the activator of the present invention, rates of $H_2O_2$ oxidation which are significantly better than those heretofore possible can be obtained with temperatures much lower than heretofore possible, thereby saving energy costs and increasing plant throughput rates where other features of the mill make this possible. Preferred temperature ranges are therefore between ambient and 130° C., preferably between ambient and 90° C. and most preferably between ambient and 60° C. For some applications, the preferred range is between about ambient and 90° C. The bleaching system of the invention will even function effectively at sub-ambient temperatures. The wide range of temperatures over which the activator will function permits the method of the present invention to be used in existing facilities and in conjunction with other pulp and paper bleaching processes without having to make special temperature adjustments for the peroxide bleaching portion of a commercial production line, other than the normally advantageous change of lowering the temperature.

The pH of the oxidation reaction can also be lowered when using the activator of the present invention. Bleaching experiments run at pH 7 with $H_2O_2$ and the oxidant activator of the present invention bleached lignin at a rate believed to be an improvement over the conventional $H_2O_2$ bleaching rate, but not at the best rate possible for the activator. Far more rapid and satisfactory rates were obtained using the pH 10. Thus, the conventional pH range of 11 to 9 need not be altered by the addition of the catalyst activator of the invention, but can be if needed to avoid the decomposition of $H_2O_2$ that is known to occur at high pH. Decomposition can also be attributed to the presence of trace metals in the bleaching solution with the peroxy compound. Sequesterants and other known stabilizers are used to reduce the likelihood of decomposition due to the presence of trace metals. The experiments set forth below demonstrate that sequesterants may also be used with the catalyst activator of the present invention.

It is further believed that bleaching by the method of the present invention will produce very favorable kappa numbers, a measure used in the pulp and paper industry to show the amount of residual lignin following bleaching. The kappa number, which should be as low as possible, is a ratio of the difference between (1) the total oxidizing equivalent necessary for 100% lignin removal and (2) the difference between the actual oxidation achieved and the total oxidizing equivalent. It is obtained by testing with potassium permanganate according to procedures well known in the pulp and paper industry.

The bleaching composition of the present invention may be used for effectively removing or significantly reducing organochlorine or color due to lignin chromophores from pulp and paper wastewaters. The oxidant and activator compound combination would decolorize the chromophores in the pulp mill effluent to remove the brown color. For environmental considerations, the oxidant in the effluent decolorizing composition is preferably a peroxy compound or ozone. Previous attempts to use ferrous ion catalyzed peroxide treatment for removal of absorbable organic halogen have proven to be unfeasible due to the very high levels of peroxide needed and the prohibitive expense associated with the use of large quantities of peroxide. The addition of the activator compound of the present invention to peroxy compounds has been demonstrated to significantly lower the level of peroxide needed for oxidation reactions. Thus, the activator/oxidant composition of the present invention is believed to be well suited to the treatment of color, organochlorine and recalcitrant carbonaceous materials in the pulp and paper wastewaters. Application at low level wastewater streams, either at the discharge site or a recycle site, are believed to be advantageous. Treatment of combined wastewaters at end-of-pipe sites have the advantage of having had the majority of degradable organic material in the effluent removed, leaving only the recalcitrant materials to be targeted by the composition of the invention. Treatment at an earlier stage upstream of the end-of pipe site has the advantage of being able to expose a greater concentration of target compounds to the composition of the invention.

Experiments are presented herein which demonstrate the usefulness of the composition for the present invention for oxidizing 2,4,6 trichlorophenol, a polychlorinated aromatic compound and environmental pollutant produced during the bleaching process when chlorine is used as the bleaching agent in pulp and paper processing. The composition of the present invention is believed to be effective for oxidizing other polychlorinated aromatic compounds as well, such as DDT, other polychlorinated phenols, dioxins, and polychlorinated biphenyls (PCBs).

As the inventive macrocyclic tetraamido metal-ligand complexes act in a catalytic fashion, the amount thereof added to the bleaching compositions is generally substoichiometric. However, it is preferred, without limitation, to add about 0.0001 to about 999,999 parts per million (ppm), more preferably 0.001 to 100,000 ppm, to the compositions of the invention.

In the Experimental Section below, selected syntheses of the preferred macrocyclic tetraamido metal ligand complexes are depicted. Additionally, tests were conducted to demonstrate the lignin bleaching capability and the sustained catalytic activity of the inventive metal complexes of these macrocyclic ligands.

2. Oxidant Compounds

The oxidant compounds, such as O transfer atoms, preferably peroxy compounds, can be an organic or inorganic compound containing the —O—O-peroxide linkage. Exemplary compounds include hydrogen peroxide, hydrogen peroxide adducts, compounds capable of producing hydrogen peroxide in aqueous solution, organic peroxides, persulfates, perphosphates, and persilicates. Hydrogen peroxide adducts include alkali metal (e.g., sodium, lithium, potassium) carbonate peroxyhydrate and urea peroxide which may liberate hydrogen peroxide in solution. Compounds capable of producing hydrogen peroxide in aqueous solution include alkali metal (sodium, potassium, lithium) perborate (mono-and tetrahydrate). The perborates are commercially available from such sources as Akzo Nev., and FMC Corporation. Alternatively, an alcohol oxidase enzyme and its appropriate alcohol substrate can be used as a hydrogen peroxide source. Organic peroxides include, without limitation, benzoyl and cumene hydroperoxides. Persulfates include potassium peroxymonosulfate (sold as Oxone®, E.I. duPont de Nemours) and Caro's acid.

An effective amount of peroxy compound is an amount sufficient to generate at least 0.001 ppm active oxygen (A.O.). While not limited thereto, it is preferred to produce from about 0.001 to about 1,000 ppm A.O. For fabric bleaching, from about 0.01 to about 50 ppm A.O. is preferred. A description of, and explanation of A.O. measurement is found in the article of Sheldon N. Lewis, "Peracid and Peroxide Oxidations, "In: Oxidation, 1969, pp. 213–258, which is incorporated herein by reference.

3. Adjuncts

The inventive macrocyclic tetraamido metal-ligand complexes, where desired, can be combined with an adjunct or base, said base comprising: builders and surfactants selected from the group consisting of anionic, nonionic, cationic, amphoteric, zwitterionic surfactants, and mixtures thereof. Other adjunct materials may be present. These compounds can also be presented in a liquid base, for a hard surface, or other surface bleaching execution. These compounds may be useful for pulp and textile bleaching processing. Each of these compounds, and adjunct materials suitable for use herein are further discussed below:

a. Builders

The builders are typically alkaline builders, i.e., those which in aqueous solution will attain a pH of 7–14, preferably 9–12. Examples of inorganic builders include the alkali metal and ammonium carbonates (including sesquicarbonates and bicarbonates), phosphates (including orthophosphates, tripolyphosphates and tetrapyrophosphates), aluminosilicates (both natural and synthetic zeolites), and mixtures thereof. Carbonates are especially desirable for use in this invention because of their high alkalinity and effectiveness in removing hardness ions which may be present in hard water, as well as their low cost. Carbonates can be used as the predominate builder. Silicates ($Na_2O:SiO_2$, modulus of 4:1 to 1:1, most preferably about 3:1 to 1:1) can also be used. Silicates, because of their solubility in water and ability to form a glassy matrix, can also be advantageously used as a binder.

Organic builders are also suitable for use, and are selected from the group consisting of the alkali metal and ammonium sulfosuccinates, polyacrylates, polymaleates, copolymers of acrylic acid and maleic acid or maleic acid or maleic anhydride, citrates and mixtures thereof b. Fillers/Diluents Fillers for the bleach composition are used to insure the correct amount or dose of cleaning activities is delivered per usage. Salts such as NaCl, $Na_2SO_4$, and borax, are preferred. Organic diluents, such as sugar, are possible. If in a liquid execution, solvents (such as, without limitation, alkanols, gycols, glycol ethers, hydrocarbons, ketones, and carboxylic acids), liquid surfactants and water could be used as diluents.

c. Surfactants

Surfactants will generally be added to bleach for removal of particular targeted soils, e.g., nonionic surfactants on oily substrates, and anionic surfactants on particulate substrates. However, generally speaking, oxidant bleach compositions may contain little or even no surfactant.

Particularly effective surfactants appear to be anionic surfactants. Examples of such anionic surfactants may include the ammonium, substituted ammonium (e.g., mono-, di-, and tri-ethanolammonium), alkali metal and alkaline earth metal salts of $C_6$–$C_{20}$ fatty acids and rosin acids, linear and branched alkyl benzene sulfonates, alkyl sulfates, alkyl ether sulfates, alkane sulfonates, olefin sulfonates, hydroxyalkane sulfonates, fatty acid monoglyceride sulfates, alkyl glyceryl ether sulfates, acyl sarcosinates and acyl N-methyltaurides. Preferred are alkylaryl sulfonated surfactants, such as alkylbenzene sulfonates.

Other preferred surfactants of use include linear ethoxylated alcohols, such as those sold by Shell Chemical Company under the brand name NEODOL. Other suitable nonionic surfactants can include other linear ethoxylated alcohols with an average length of 6 to 16 carbon atoms and averaging about 2 to 20 moles of ethylene oxide per mole of alcohol; linear and branched, primary and secondary ethoxylated, propoxylated alcohols with an average length of about 6 to 16 carbon atoms and averaging 0–10 moles of ethylene oxide and about 1 to 10 moles of propylene oxide per mole of alcohol; linear and branched alkylphenoxy (polyethoxy) alcohols, otherwise known as ethoxylated alkylphenols, with an average chain length of 8 to 16 carbon atoms and averaging 1.5 to 30 moles of ethylene oxide per mole of alcohol; and mixtures thereof.

Further suitable nonionic surfactants may include polyoxyethylene carboxylic acid esters, fatty acid glycerol esters, fatty acid and ethoxylated fatty acid alkanolamides, certain block copolymers of propylene oxide and ethylene oxide, and block polymers of propylene oxide and ethylene oxide with propoxylated ethylene diamine. Also included are such semi-polar nonionic surfactants like amine oxides, phosphine oxides, sulfoxides, and their ethoxylated derivatives.

Suitable cationic surfactants may include the quaternary ammonium compounds in which typically one of the groups linked to the nitrogen atom is a $C_{12}$–$C_{18}$ alkyl group and the other three groups are short chained alkyl groups which may bear substituents such as phenyl groups.

Further, suitable amphoteric and zwitterionic surfactants which contain an anionic water-solubilizing group, a cationic group and a hydrophobic organic group may include amino carboxylic acids and their salts, amino dicarboxylic acids and their salts, alkylbetaines, alkyl aminopropylbetaines, sulfobetaines, alkyl imidazolinium derivatives, certain quaternary ammonium compounds, certain quaternary phosphonium compounds and certain tertiary sulfonium compounds.

Further examples of anionic, nonionic, cationic and amphoteric surfactants which may be suitable for use in this invention are depicted in Kirk-Othmer, Encyclopedia of Chemical Technology, Third Edition, Volume 22, pages 347–387, and McCutcheon's Detergents and Emulsifiers, North American Edition, 1983, which are incorporated herein by reference.

d. Chelating Agents

In some of the compositions herein, it is especially preferred to include a chelating agent, most preferably in laundry bleaching applications, an aminopolyphosphonate, and in pulp bleaching applications, polycarboxylate. These chelating agents assist in maintaining the solution stability of the oxidant in order to achieve optimum performance. In this manner, they are acting to chelate free heavy metal ions. The chelating agent is selected from a number of known agents which are effective at chelating free heavy metal ions. The chelating agent should be resistant to hydrolysis and rapid oxidation by oxidants. Preferably, it should have an acid dissociation constant ($pK_a$) of 1–9, indicating that it dissociates at low pH's to enhance binding to metal cations. The most preferred chelating agent for laundry bleaching applications is an aminopolyphosphonate which is commercially available under the trademark DEQUEST, from Monsanto Company. Examples thereof are DEQUEST 2000, 2041, 2060 and 2066. A polyphosphonate, such as DEQUEST 2010, is also suitable for use. Other chelating agents, such as ethylenediaminetetraacetic acid (EDTA) and nitrilotriacetic acid (NTA) are preferred for pulp bleaching applications. Still other new, preferred chelating agents are new propylenediaminetetraacetates, such as Hampshire 1,3 PDTA, from W. R. Grace, and Chel DTPA 100#F, from Ciba-Geigy A.G. Mixtures of the foregoing may be suitable. Effective amounts of the chelating agent range from 1–1,000, more preferably 5–500, most preferably 10–100 ppm chelating agent in the wash liquor.

e. Other Adjuncts:

The standard oxidant bleach adjuncts can be included in the present invention.

These include enzymes are especially desirable adjunct materials in oxidant bleach products. However, it may be preferred to include an enzyme stabilizer.

Proteases are one especially preferred class of enzymes. They are selected from acidic, neutral and alkaline proteases. The terms "acidic," "neutral," and "alkaline," refer to the pH at which the enzymes activity is optimal. Examples of neutral proteases include MILEZYME (available from Miles Laboratory) and trypsin, a naturally occurring protease. Alkaline proteases are available from a wide variety of sources, and are typically produced from various microorganisms (e.g., Bacillis subtilis). Typical examples of alkaline proteases include MAXATASE and MAXACAL from International BioSynthetics, ALCALASE, SAVINASE and ESPERASE, all available from Novo Industri A/S. See also Stanislowski et al., U.S. Pat. No. 4,511,490, incorporated herein by reference.

Further suitable enzymes are amylases, which are carbohydratehydrolyzing enzymes. It is also preferred to include mixtures of amylases and proteases. Suitable amylases include RAPIDASE, from Societe Rapidase, MILEZYME from Miles Laboratory, and MAXAMYL from International BioSynthetics.

Yet other suitable enzymes are lipases, such as those described in Silver, U.S. Pat. No. 3,950,277, and Thom et al., U.S. Pat. No. 4,707,291, both incorporated herein by reference.

Still further enzymes of interest herein are peroxidases, such as horseradish peroxidase, and those disclosed in International Patent Publication WO 93/24628, incorporated herein by reference. Mixtures of any of the foregoing hydrolases are desirable, especially protease/amylase blends.

Additionally, optional adjuncts include dyes, such as Monastral blue and anthraquionone dyes (such as those described in Zielske, U.S. Pat. No. 4,661,293, and U.S. Pat. No. 4,746,461).

Pigments, which are also suitable colorants, can be selected, without limitation, from titanium dioxide, ultramarine blue (see also, Chang et al., U.S. Pat. No. 4,708,816), and colored aluminosilicates.

Fluorescent whitening agents are still other desirable adjuncts. These include the stilbene, styrene, and naphthalene derivatives, which upon being impinged by ultraviolet light, emit or fluoresce light in the visible wavelength.

Additional organic bleach activators can be added, including, but not limited to, esters (see Fong et al., U.S. Pat. No. 4,778,618 and Rowland et al., U.S. Pat. No. 5,182,045), ketones, imides (See Kaaret, U.S. Pat. No. 5,478,569) and nitrites, each of which are incorporated herein by reference.

The additives may be present in amounts ranging from 0–50%, more preferably 0–30%, and most preferably 0–10%. In certain cases, some of the individual adjuncts may overlap in other categories. However, the present invention contemplates each of the adjuncts as providing discrete performance benefits in their various categories.

EXPERIMENTAL SECTION

Syntheses of Oxidatively Robust Tetraamido Ligands.

Materials. All solvents and reagents were reagent grade (Aldrich, Aldrich Sure-Seal, Fisher) and were used as received. Microanalyses were performed by Midwest Microlabs, Indianapolis, Ind.

Mass Spectrometry. Electrospray ionization mass spectra were acquired on a FINNIGAN-MAT SSQ700 (San Jose, Calif.) mass spectrometer fitted with an ANALYTICA OF BRANFORD electrospray interface. Electrospray voltages of 2400–3400 V were utilized. Samples were dissolved in either acetonitrile or dichloromethane at concentrations of approximately 10 pmol/ml and were introduced into the ESI interface prior to data acquisition by direct infusion at a flow rate of 1 l/min and were introduced prior to data acquisition. Positive ion electron impact ionization (70 ev) MS experiments were performed on a FINNIGAN-MAT 4615 quadrupole mass spectrometer in conjunction with an INCOS data system. The ion source temperature was 150° C. and the manifold chamber temperature was 100° C. Sample introduction was by means of a gas chromatograph or a direct insertion probe. Positive ion fast atom bombardment mass spectra were acquired on a FINNIGAN-MAT 212 magnetic sector instrument in combination with an INCOS data system. The accelerating voltage was 3 kV and the ion source temperature was about 70° C. An ION TECH saddle field fast atom gun was employed with xenon at 8 keV. Thio-glycerol was utilized as the FAB matrix. Positive ion electron impact ionization (70 eV) MS/MS experiments were performed on a FINNIGAN-MAT TSQ/700 tandem quadrupole mass spectrometer. Sample introduction was by means of a direct insertion probe. The ion source was maintained at 150° C. and the manifold chamber was held at 70° C. Collision-induced dissociation (CID) was achieved by introducing argon into the center rf-only collision octapole until the pressure in the manifold reached $0.9–2.5×10^{-6}$ Torr. The nominal ion kinetic energy for CID product ions was <35 eV (laboratory reference). High resolution data were obtained on a JEOL JMS AX-505H double focusing mass spectrometer in the EB configuration using a resolution of 7500. Sample introduction was by means of a gas chromatograph or direct insertion probe. During mass spectral acquisition, perfluorokerosene was introduced into the ion source by means of a heated inlet. Exact mass assignments introduced into the ion source by means of a heated inlet. Exact mass assignments were obtained by computer-assisted interpolation from the masses of perfluorokerosene. GC/MS conditions: column, 20 m×0.25 mm DB-1701 (J & W Scientific); carrier gas, helium with a linear velocity of 40 cm/sec; injector, 125° C.; column temperature, 35° C. for 3 min, followed by an increase at 10° C./min to 100° C.; injection, split mode, appx. 50:1 ratio.

Spectroscopic Methods. 300 MHz $^1$H NMR spectra and 75 MHz $^{13}$C NMR spectra were obtained on an IBM AF300 instrument using an OXFORD Superconducting magnet system, data acquisition was controlled by BRUKER software. Infrared spectra were obtained on a MATTSON GAL-AXY Series 5000 FTIR spectrometer controlled by a MACINTOSH II computer. UV/vis spectra were obtained on a HEWLETT PACKARD 8452A spectrophotometer driven by a ZENITH Z-425/SX computer. Conventional X-Band EPR spectra were recorded on a BRUKER ER300 spectrometer equipped with an OXFORD ESR-900 helium flow cryostat. Mossbauer spectra were obtained on constant acceleration instruments and isomeric shifts are reported relative to an iron metal standard at 298 K. In order to avoid orientation of polycrystalline samples by the applied magnetic field, the samples were suspended in frozen nujol.

Syntheses of Macrocyclic Tetraamido-N Donors Ligands

General Reaction Scheme

Depicted below is the preferred reaction sequence for synthesizing the inventive macrocyclic tetraamido metal ligand complexes:

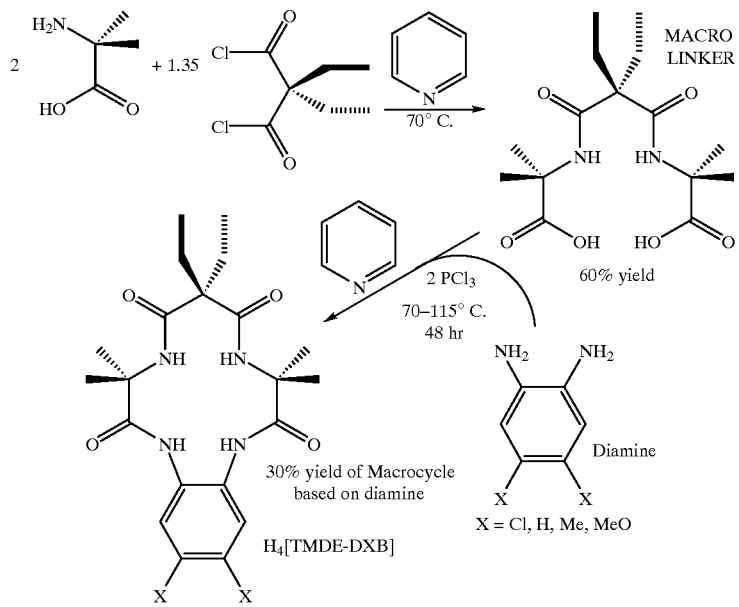

An α-amino carboxylic acid is mixed with an activated malonate in pyridine at temperatures less than 70° C. After the selective double coupling reaction is complete, 72–144 hrs., the MACRO LINKER (A-L-A) is isolated. In a second step, a diamine, preferably an o-phenylene diamine, is added to a pyridine solution of the MACRO LINKER in the presence of a coupling agent, preferably PCl$_3$ or pivaloyl chloride. The ring closure (a double coupling) reaction is allowed to proceed at reflux for 48–110 hrs., and then the desired macrocyclic tetraamide is isolated in good yield.

In the following Examples 1–25, various portions of the reaction steps are portrayed. Examples 26–39 demonstrate performance attributes and advantages of the invention for oxidation reactions involving lignin bleaching and dye bleaching.

EXAMPLE 1

Macro Linker Intermediate (A-L-A) synthesis, from a α-methyl alanine and diethyl malonyl dichloride (a Tetramethyl Diethyl substituted intermediate).

A two-neck flask (1 L) fitted with a pressure equalizing addition funnel (250 mL) and a septum is placed under N$_2$ α-amino isobutyric acid (i.e. α-methyl alanine) (20.62 g, 0.2 mol) and dry pyridine (250 mL, dried over 4 Å mol sieves) are added to the flask and heated 60–70° C. with stirring, then diethyl malonyl dichloride (23.23 mL, 0.135 mol)

dissolved in dry pyridine (100 mL, dried over 4 A mol sieves) is added to the addition funnel. The contents of the addition funnel are added (dropwise, 1 h) to the reaction and the acylation allowed to proceed (60–70° C., 30–36 h) under $N_2$ or with a drying tube fitted. Once the acylation is complete the reaction is quenched by adding $H_2O$ (30 mL) and stirring (60–70° C., 24 h). The solvent volume is reduced on the rotary evaporator to give an oil, then HCl (conc., ca. 25 mL) is added to a final pH of 2–3. The hot solution is set in the refrigerator (4° C., 15 h), and the resulting tan product collected by frit filtration, and washed thoroughly with acetonitrile (2×100 mL). The air-dried white product (16.5–19.8 g, 50–60% yield) should be stored in a dessicator. This product is usually pure enough for ring closure reactions, but recrystallization may occasionally be required. Characterization: $^1$H NMR spectrum ($d^5$-pyridine) δ [ppm]: 8.9 (s, 2H, NH amide); 2.2 (q, 4H); 1.8 (s, 12H); 1.2 (t, 6H). IR(Nujol mull):n [cm$^{-1}$]=3310 (amide NH); 1721 (carboxylic CO); 1623 (amide CO). Anal. Calcd for $C_{15}H_{21}N_2O_6$; C, 54.53; H, 7.93; N, 8.48. Found: C, 54.48; H, 7.88; N, 8.47.

EXAMPLE 2

Large Scale, Macro Linker Intermediate (A-L-A) synthesis, from a-methyl alanine and diethyl malonyl dichloride (a TMDE substituted intermediate).

A two-neck flask (2 L, RB+Claisen) fitted with a pressure equalizing addition funnel (250 mL) and septa, is placed under $N_2$ a-aminoisobutyric acid (i.e. a-methyl alanine) (90.3 g, 0.9 mol) is added, anhydrous pyridine (1.4 L, sure seal) is cannulated into the flask and the reaction mix heated to 45–55° C. and stirred. Pyridine (100 mL, sure seal) and then diethyl malonyl dichloride (104.4 mL, 0.61 mol) are cannulated into the addition funnel. The contents of the addition funnel are added (dropwise, 3–4 h) to the reaction, the addition funnel is then removed, and the acylation allowed to proceed (55–65° C., 120–130 h) under $N_2$. Once the acylation is complete the reaction is quenched by adding $H_2O$ (100 mL) and stirring (60–70° C., 24–36 h). The solvent volume is reduced on the rotary evaporator to give an oil, then HCl (conc., ca. 110 mL) is added to a final pH of 2–3. The hot solution is set in the refrigerator (4° C., 15 h), and the resulting tan product collected by frit filtration, and washed thoroughly with acetonitrile (700 mL, 150 mL) by stirring in an erlenmeyer flask. The air-dried white product (87.9 g, 60% yield), is crushed in a mortar and pestle and stored in a dessicator. The large scale reaction amide intermediate product is more likely to need recrystallization before use in ring closure reactions.

EXAMPLE 3

Recrystallization of the TMDE Substituted Intermediate

Crude TMDE intermediate from Example 2 (50.4 g., 0.153 mol) is dissolved in $H_2O$ (500 mL, deionized) by adding $Na_2CO_3$ (16.2 g, 0.153 mol) in three aliquots slowly and carefully to avoid excessive frothing, with good stirring and mild heating. The solution is brought to a boil, filtered and acidified with HCl (conc., 30 mL, 0.36 mol). The solution is allowed to cool (overnight, 4° C.) and the white precipitate filtered off and washing with acetonitrile (250 mL). The air dried product (38.8–45.4 g, recryst. yield 77–90%) should be stored in a dessicator.

EXAMPLE 4

TMDM Substituted Intermediate (A-L-A)

The synthesis of the TMDM substituted intermediate is identical to that for the TMDE substituted intermediate in Example 2 with the following exceptions, dimethyl malonyl dichloride (17.8 mL, 0.135 mol) is substituted for diethyl malonyl dichloride, and the reaction temperature must be decreased to 55–65° C. due to the lower boiling point of the acylating agent. The yield of the TMDM intermediate is 45–60%. Characterization: $^1$H NMR ($d^5$ pyridine, δ [ppm]); 9/2–9.8 br s, 2 H (carboxylic OH), 8.23 s, 2 H (amide), 1.87 s 12 H ($CH_3$), 1.74 s 6 H ($CH_3$). IR (nujol/NaCl) v[cm$^{-1}$]; 3317.0 (amide NH); 1717.9 (carboxylic CO); 1625.7 (amide CO). Anal. (dried at 100° C.) Calcd. for $C_{13}H_{22}N_2O_6$; C 51.63, H 7.34, N 9.27. Found; C 51.64, H 7.35, N 9.33.

EXAMPLE 5

Recrystallization of TMDM Substituted Intermediate

Crude TMDM intermediate was recrystallized in the same manner as the TMDE substituted intermediate. Due to the slightly higher water solubility of the TMDM substituted intermediate a little less $H_2O$ should be employed.

EXAMPLE 6

Di CyHex Di Ethyl (DiCyHexDE) Substituted Intermediate

A round bottom flask (500 mL), is charged with 1-amino-1-cyclohexane carboxylic acid (15 g, 0.1 mol), then fitted with a pressure equalizing addition funnel (40 mL), capped with a septum, and purged with nitrogen. Anhydrous pyridine (300 mL) is cannulated into the reaction flask through the addition funnel, and 20 mL into the addition funnel. Start heating the system and stabilize the temperature at 60° C. Once 60° C. is reached, one-third of the total diethyl malonyl dichloride to be utilized in the reaction (i.e. 6 mL, 0.033 mol) is added via syringe to the addition flask. The mixture of pyridine/diethyl malonyl dichloride is added dropwise to the reaction and the acylation allowed to proceed for 12 hours. A second (6 mL, 0.033 mol) and third aliquot (6 mL, 0.033 mol) are added at 12 hour intervals. After all of the acylating agent has been added and allowed to react (total reaction time 48–56 h), 20 mL of water is added dropwise to the reaction. The reaction is heated for an additional 24 hours to ring open the mono and bis oxazalone intermediates and yield the diamide dicarboxylic acid. Removal of the pyridine by rotary evaporation yields a pale yellowish tan sludge which is acidified to pH 2 with HCl(conc.). The crude product is collected by filtration, washed with acetonitrile and air dried to yield the white DiCyHexDE substituted intermediate (16 g, 74%). Characterization: $^1$H NMR ($d^5$-pyridine) δ [ppm]: 8.30 (s, 2H, NH amide), 2.60 (m, 4 H, cyhex), 2.25 (q,4 H, ethyl $CH_2$), 2.15 (m, 4 H, cyhex), 1.8–1.5 (m, 10 H, cyhex), 1.25 (m, 2 H, cyhex), 1.20 (t, 6H, ethyl $CH_3$). $^{13}$C NMR broadband decoupled ($d^5$-pyridine) δ [ppm]: 178.0, (carboxylic CO), 174.3 (amide CO), 60.5 (cyhex quat), 59.4 (malonyl quat), 33.0 (cyhex a $CH_2$), 30.3 (ethyl $CH_2$) 26.0 (cyhex g $CH_2$), 22.3 (cyhex b $CH_2$), 9.9 (ethyl $CH_3$). IR (nujol/NACl) v [cm-$^1$]: 3307 (amide NH); 3150 (sh, br, m, amide NH/carboxylic OH), 3057 (s, str, H bonded amide NH/carboxylic OH), 1717 (s, str, carboxylic CO); 1621 (s, str, amide CO). Anal. Calcd for $C_{21}H_{34}N_2O_6$: C, 61.44; H, 8.35; N, 6.82. Found: C, 61.41; H, 8.38, N, 6.90%.

EXAMPLE 7

Di CyHex Diethyl Mono Oxazalone

Failure to quench the Di CyHex Di Ethyl Intermediate Reaction (with heat & water, see above) at a stoichiometry of 1.35 diethyl malonyl dichloride; 2 CY Hex amino acid, leads to a mixture of the DiCyHexDE substituted intermediate and mono oxazalone products. The DiCyHexDE Mono Oxazalone product is moderately soluble in boiling cyclohexane while the cyclohexyl amide intermediate is not, allowing for a simple separation of the product mixture, ca. 10 g of mixed amide intermediate and mono oxazalone containing some residual $CH_2Cl_2$ was boiled with vigorous stirring in 400–500 mL cyclohexane. The insoluble DiCyHexDE substituted intermediate product was collected by hot gravity filtration while the mono oxazalone product crystallized out gradually as the cyclohexane solution cooled and evaporated. Yield amide intermediate ca. 6 g, yield mono oxazalone ca. 4 g. Characterization of the mono oxazalone: $^1$H NMR (d$^5$-pyridine) δ [ppm]: 9.7 (s, 1H, amide NH), 2.7–1.6 (unresolved Cy Hex groups), 1.05 (t, 6 H, ethyl $CH_3$). IR (nujol/NaCl) [cm$^{31}$ $^1$]: 3309 (sh, w, amide NH), 3229 (s, str, H bonded amide NH/carboxylic OH), 3166 (s, str, H bonded amide NH/carboxylic OH), 3083 (s, str, H bonded amide NH/carboxylic OH), 1834 (s, str, oxaz C=O), 1809 (s, m, H bonded oxaz C=O), 1743 (s, str, carboxylic CO), 1663 (s, str, oxaz C=N), 1639 (s, br, str, amide CO). Anal. Calcd for $C_{21}H_{32}N_2O_5$ $(C_6H_{12})$0.25: C, 65.35; H, 8.53; N, 6.77. Found: C, 65.07; H 8.67: N, 6.68%. Presence of solvate cyclohexane was confirmed by $^{13}$C NMR.

Macrocyclization Reactions

Examples of several synthetic routes for the preparation of macrocyclic tetraamido metal ligand complexes follow.
Phosphorus Trichloride Coupling Phosphorus trichloride coupling of the amide-containing intermediate (A-L-A) to aromatic 1,2-diamines yields macrocyclic tetraamides safely, cheaply and in high yield. Two distinct variations of the $PCl_3$ coupling method are useful, the differences relate to the order of addition and choice of reagents utilized. These methods are applicable to the preparation of a wide variety of different macrocycles with different electronic substituents present on the bridge diamine, or steric substituents present on the amide intermediate, primarily because of the parallel incorporation of the macro linker type of amide intermediates into all of the syntheses.

EXAMPLE 8

A. Macrocycle Synthesis via $PCl_3$ Coupling

A long neck flask (250 mL) is charged with the amide intermediate of Examples 2–7, (10 mmol) a stir bar and then baked in the oven (80–100° C., 30–45 mins). The hot flask is placed under $N_2$, aryl diamine (10 mmol) is added and anhydrous pyridine (50 mL, sure seal) cannulated in. The flask is heated (50–60° C.) and $PCl_3$ (d=1.574 g/mL, 1.72 mL, 20 mmol) syringed in as quickly as possible without excessive refluxing. This is an exothermic reaction, so caution should be used. The temperature is then increased to reflux or just below reflux (100–115° C.) and the reaction allowed to proceed under $N_2$ (48 h). After the acylation is complete, the contents of the flask are acidified with HCl (1 eq., ca. 60 mL) to a final pH 2. The mixture is transferred to an erlenmeyer (water is used to rinse the flask) and stirred with $CH_2Cl_2$ (300 mL, 2–3 h), then extracted with additional $CH_2Cl_2$ (2×150 mL). The combined organic layers are washed with dilute HCl (0.1 M, 2×100 mL) followed by dilute aqueous $Na_2CO_3$ (2×5 g/100 mL). The organic solvents are removed on the rotary evaporator to yield crude product (30%). The weight of crude product is usually equivalent to the initial weight of diamine.

B. Macrocycle Synthesis via $PCl_3$, Coupling

A long neck flask (250 mL) is charged with $MgSO_4$ (5 g), a stir bar, aryl diamine (10 mmol) and pyridine (50 mL, dried over 4 A mol sieves) then placed under $N_2$ $PCl_3$ (d=1.754 g/mL, 1.72 mL, 20 mmol) is added via syringe and the mixture brought to reflux for 30 mins, an orange/yellow precipitate forms. The mixture is cooled somewhat, an amide intermediate (10 mmol) is added, then the mixture is refluxed under $N_2$ (115° C., 48 h). After the acylation is complete, the contents of the flask are acidified with HCl (1 eq., ca. 60 mL) to a final pH 2. The mixture is transferred to an erlenmeyer and stirred with $CH_2Cl_2$ (2×150 mL). The combined organic layers are washed with dilute HCl (0.1 M, 2×100 mL) followed by dilute $Na_2CO_3$ (2×5 g/100 mL). The organic solvents are removed on the rotary evaporator to yield crude product (30%). The weight of crude product is usually equivalent to the initial weight of diamine.

Note: For larger scale macrocyclization reactions, the ring closure times are increased to 4–5 days at reflux, and most of the pyridine present at the end of the reaction is removed via rotary evaporation prior to acidification.

EXAMPLE 9

TMDE-DCB from TMDE Intermediate+DCB Diamine 1,2-Diamino-4,5 dichlorobenzene (1.77 g, 10 mmol) was utilized as the aryl diamine with TMDE amide intermediate (3.3 g, 10 mmol) in the $PCl_3$ method A or B macrocyclization reaction. The crude macrocyclic product (2.7 g) was recrystallized from a minimum amount of hot 95% EtOH by evaporation to yield pure TMDE-DCB (1.5 g, 32%). Characterization: $^1$H NMR ($CD_2Cl_2$) δ [ppm]:7.65 (s, 1 H, ArH), 7.35 (s, 2 H, amide NH), 6.45 (s, 2H, amide NH), 1.90 (q, 4 H, ethyl $CH_2$), 1.57 (s, 12 H, $RCH_3$), 0.85 (t, 6H, ethyl $CH_3$). IR (nujol/NaCl) v[cm$^{-1}$]: 3454 (trace ROH), 3346 (br, amide NH), 1706&1688&1645 (amide CO). Anal. Calcd. for $C_{21}H_{28}Cl_2N_4O_4$; C, 53.51; H, 5.99; N, 11.89. Found C, 53.58; H, 6.09; N, 11.89.

EXAMPLE 10

TMDE-B from TMDE Intermediate+B Diamine 1,2-Diaminobenzene (i.e, o-phenylene diamine)(1.08 g, 10 mmol) was utilized as the aryl diamine with the TMDE amide intermediate (3.3 g, 10 mmol) in the PCl, method A or B macrocyclization reaction. The crude macrocyclic product (1.5 g) was recrystallized from a minimum amount of hot 95% EtOH by evaporation to yield pure TMDE-B (25% from diamine). Characterization: $^1$H NMR ($CDCl_3$) δ [ppm]; 7.55 (m, 2 H, ArH), 7.48 (s, br, 2 H, aryl amide NH), 7.17 (m, 2 H, ArH), 6.46 (s, br, 2 H, alkyl amide NH), 2.07 (m, br, 4 H, ethyl $CH_2$), 1.60 (s, 12 H, $RCH_3$), 0.89 (t, 6 H, ethyl $CH_3$). IR (nujol/NaCl) [cm$^1$]; 3395, 3363 (amide NH), 1702, 1680, 1652, 1635 (amide CO). Anal. Calcd. for $CH_{21}H_{10}N_4O_4H_2O$: C, 59.98; H, 7.67; N, 13.32. Found: C, 60.18; H, 7.20; N, 13.18.

EXAMPLE 11

TMDE-DMB from TMDE Intermediate+DMB Diamine 1,2-Diamino-4,5-Dimethylbenzene (1.36 g, 10 mmol) was utilized as the aryl diamine with TMDE intermediate (3.3 g, 10 mmol) in the $PCl_3$ method A or B macrocyclization reaction. The crude macrocyclic product (1.6 g) was recrystallized from a minimum amount of hot 95% EtOH by evaporation to yield pure TMDE-DMB (25% from diamine). Characterization: $^1$H NMR (DMSO d$^6$) δ [ppm]: 8.00 (s, 2 H, amide NH), 7.67 (s, 2 H, amide NH), 7.28 (s, 2 H, ArH), 2.17 (s, 6 H, aryl CH$_3$), 1.99 (q, 4 H, ethyl CH$_2$), 1.46 (s, 12 H, RCH$_3$), 0.75 (t, 6 H, ethyl CH$_3$). Ir (nujo/NaCl) ν [cm$^{-1}$]: 3446 (s, m, trace ROH), 3362 (s, str, amide NH), 3348 (sh, m, amide NH), 3332 (s, str, H amide NH), 1696 (amide CO), 1679 (amide CO), 1651 (amide CO), 1641 (amide CO), 1584 (s, m/w, aryl ring/amide). Anal. Calcd. for C$_{23}$H$_{34}$N$_4$O$_4$: C. 64.16; H, 7.96; N, 13.01, Found: C, 64.09, 64.28; H, 8.04, 7.92; N, 12.86, 13.04.

EXAMPLE 12

TMDE-DMOB from TMDE Intermediate+DMOB Diamine 1,2-Diamino-4,5-Dimethoxybenzene. 2 HBr (5.0 g, 15 mmol) prepared as above was utilized as the aryl diamine directly with the TMDE intermediate (5.0 g, 15 mmol) in a 1.5 scale PCl$_3$ method A or B macrocyclization reaction. The crude macrocyclic product (3.57 g) was recrystallized from a minimum amount of hot 80–85% EtOH (1 g/40 mL) by evaporation to yield pure TMDE-DMOB (30% from diamine). Characterization: $^1$H NMR (CD$_2$Cl$_2$) δ [ppm]: 7.26 (s, 2 H, amide NH), 7.01 (s, 2 H, ArH), 6.41 (s, 2 H, amide NH), 3.80 (s, 6H, aryl OCH$_3$), 2.07 (q, br, 4 H, ethyl CH$_2$), 1.54 (s, 12 H, RCH$_3$), 0.90 (t, 6 H, ethyl CH$_3$). IR (nujo/NaCl) ν [cm$^{-1}$]: 3451 (s, m, H bonded H$_2$O), 3391, 3347 (amide NH), 1695, 1670, 1655 (amide CO). Anal. Calcd. for C$_{23}$H$_{34}$N$_4$O$_6$, (H$_2$O)$_{0.33}$: C, 58.96; H, 7.46; N, 11.96, Found (ESU); C, 58.90 H, 7.26; N, 11.76. Presence of solvate H$_2$O was confirmed by $^1$H NMR and IR.

EXAMPLE 13

TMDE-Nap from TMDE Intermediate+Nap Diamine 4,5 Diamino Napthalene (1.68 g, 10 mmol) was utilized as the aryl diamine with the TMDE intermediate (3.3 g, 10 mmol) in the PCl$_3$ method A or B macrocyclization reaction. Unoptimized yield was 15–20% from diamine. $^1$H NMR (CDCl$_3$) δ [ppm]: 8.05 (s, 2 H, ArH a ring), 7.75 (m, 2H, ArH b ring), 7.55 (s, 2 H, Ar amide NH), 7.35 (m, 2H, ArH b ring), 6.45 (s, 2 H, alkyl amide NH), 2.15 (m, br, 4 H, ethyl CH$_2$,), 1.65 (s, 12 H, RCH$_3$), 0.90 (t, 6 H, ethyl CH$_3$).

EXAMPLE 14

TMDM-DCB from TMDM Intermediate+DCB Diamine 1,2-Diamino-4,5-Dichlorobenzene (1.77 g, 10 mmol) was utilized as the diamine with TMDM amide intermediate (3.02 g, 10 mmol) in the PCl$_3$, method A or B macrocyclization reaction. The crude macrocycle (1.33 g, 30%) was recrystallized from a minimum of hot n-propanol by evaporation, 1st crop recrystallization yield was 60%. Characterization: $^1$H NMR δ [ppm]: 7.69 (s, 2 H, ArH), 7.39 (s, 2 H, amide NH), 6.44 (s, 2 H, amide NH), 1.58 (s, 12 H, arm methyls), 1.53 (s, 6 H, malonate methyls), small n-propanol peaks were noted. IR (nujol/NaCl) ν [cm$^{-1}$]: 3503 (s, br, m-w, n-propanol OH, 3381 (sh, m, amide NH), 3338 (s, str, amide NH), 1689 (s, str, amide CO), 1643 (s, str, amide CO). Anal. Calcd. for C$_{19}$H$_{24}$N$_4$O$_4$Cl$_2$. (C$_3$H$_8$O)$_{0.2}$: C, 51.70; H, 5.57, N, 12.30%. Found C, 51.69; H, 5.63; N, 12.33%.

EXAMPLE 15

TMDM-DMOB and TMDM-B from TMDM Intermediate+DMOB or B Diamine

The TMDM intermediate has also been used to synthesize TMDM-B and TMDM-DMOB according to the same method and with similar results to those obtained in example 14 for the dichloro derivative. $^1$H NMR data for TMDM-DMOB in CDCl$_3$ d [ppm]: 7.65 (s, 2H, amide NH), 7.21 (s, 2 H, aryl CH), 6.72 (s, 2 H, amide NH), 4.00 (s, 6 H, methoxy CH$_3$), 1.76 (s, 12 H, arm methyls), 1.58 (s, 6 H, malonate methyls). $^1$H NMR data for TMDM-B in d$^5$ pyridine δ [ppm]: 8.55 (s, 2 H, amide NH), 8.40 (s, 2 H, amide NH), 7.81 (m, 2H, ArH aa'bb'), 7.10 (m, 2 H, ArH aa'bb'), 1.77 (s, 12 H, arm methyls), 1.73 (s, 6 H, malonate methyls). The amide peaks tend to shift a few tenths of a ppm in the presence of impurity species such as water, acids, etc.

EXAMPLE 16

DiCyHexDE-DCB from DiCyHexDE Intermediate+DCB Diamine 1,2-Diamino-4,5-Dichlorobenzene (1.77 g, 10 mmol) was utilized as the aryl diamine with Di Cy Hex DE intermediate (3.3 g, 10 mmol) in the PCl$_3$, method A or B macrocyclization reaction. Due to the increased steric hindrance an increased ring closure reaction time is recommended (3–4 days as opposed to the usual 48 h). Cy Hex Oxazalones formed as a side product during the reaction are not removed by the acid base workup, so it is necessary to triturate/wash the initially isolated CH$_2$Cl$_2$ soluble product with pentane to remove the oxazalones. Evaporation of the pentane washes allows for recycling of the oxazalones. The crude pentane insoluble product was recrystallized by dissolving in CH$_2$Cl$_2$ or CHCl$_3$, adding cyclohexane until slightly cloudy and then evaporating in air (1–2 days) to yield the white microcrystalline DiCyHexDE-DCB product, which was collected by filtration (1.38 g, 25% from diamine). Recrystallization from hot neat toluene with evaporation also appears promising. Characterization: $^1$H NMR (CDCl$_3$) δ [ppm]: 7.70 (s, 2 H, ArH), 7.45 (s, 2 H, amide NH), 6.45 (s, 2 H, amide NH), 2.35 (m, br, 4 H, cyhex), 2.00 (m, br, >>8 H, cyhex/ethyl CH$_2$), 1.70 (m, br, >>8 H, cyhex), 1.30 (m, br, >>4 H, cyhex), 0.90 (t, 6 H, ethyl CH$_3$). Anal. (Dried at 100° C.) Calcd. for C$_{27}$H$_{36}$Cl$_2$N$_4$O$_4$, (C$_6$H$_{12}$)$_{0.2}$: C, 59.60; H, 6.81; N, 9.86, Found: C, 59.60; H, 6.77; N, 9.77. Presence of solvent cyclohexane was confirmed by $^1$H and $^{13}$C NMR.

EXAMPLE 17

DiCyHexDE-B from DiCyHexDE Intermediate+B Diamine 1,2-Diaminobenzene (ortho-phenylene diamine, 1.08 g, 10 mmol) was utilized as the aryl diamnine in a preparation analogous to that for DiCyHexDE-DCB, to yield DiCyHexDE-B (1.25 g, 26% from diamine). Characterization: $^1$H NMR (DC$_3$CN) δ [ppm]: 7.62 (s, 2 H, aryl amide NH), 7.51 (m, 2 H, ArH), 7.18 (m, 2 H, ArH), 6.71 (s, 2 H, alkyl amide NH), 2.12 (m, 6H, Cyhex), 1.85 (q & m, ethyl CH$_2$ & cyhex), 1.62 (m, cyhex), 1.37 (m, cyhex), 0.90 (t, 6 H, ethyl CH$_3$), 0.85 (m, cyhex). IR (nujol/NaCl) ν [cm$^{-2}$]: 3750 (s, m, H$_2$O), 3385 (s, str, amide NH), 314 (s, str, amide NH), 3258 (s, m, br, H bonded amide NH), 1694 (s, str, amide CO), 1651 (s, str, amide CO), 1594 (s, m, aryl ring/amide).

EXAMPLE 18

DiCyHexDE Bis Oxazalone

This product was obtained as a byproduct of the PCl$_3$, macrocyclization reaction of DiCyHexDE Amide Intermediate with o-phenylene diamine. The bis oxazalone is not removed by the acid base workup (it is a neutral molecule and very organic soluble). Washing of the crude macrocyclic/oxazalone product with pentane extracts most of the bis oxazalone into the pentane. Air evaporation of the pentane layer yields the pure bis oxazalone as large (1 cm×1 cm×0.5 cm) transparent prisms. Due to the bulky hydrophobic CyHex groups this oxazalone is much more resistant to hydrolysis than the corresponding methyl derivative. Characterization of the bis oxazalone: $^1$H NMR (CD$_3$CN) δ [ppm]: 2.05 (q, 4 H, ethyl CH$_2$), 1.8–1.4 (Unresolved Cy Hex Groups), 0.88 (t. t H, ethyl CH$_3$). $^{13}$C NMR broadband decoupled (CD$_3$CN) δ [ppm]: 181.0 (oxaz (C=O), 162.7 (oxaz C=N), 69.0 (oxaz cyhex quat), 49.0 (malonate quat), 34.3 (cyhex a methylenes), 25.5 (cyhex g methylenes), 24.9 (malonate methylenes), 21.8 (cyhex b methylenes), 8.3 (ethyl CH$_3$). IR (nujol/NaCl) ν [cm:$^{-1}$]: 1822 (s, str, br, oxaz C=O), 1662 (s, str, oxaz C=N). Anal. (Dried at 50° C.) Calcd. for C$_{21}$H$_{30}$N$_2$O$_4$: C, 67.36; H, 8.07; N, 7.48, Found: C, 67.26; H, 8.15; N, 7.64.

Syntheses of Chelate Complexes

EXAMPLE 19

[Et$_4$N]2 and [Et$_4$N]3, [the tetraethylammonium salts of iron(III) chloro TMDE-DCB dianion [Fe (Cl)DCB]$^{2-}$ and iron(III) aquo TMDE-DCB monoanion, [Fe (H$_2$O) DCB]$^{31}$ respectively].

The parent macrocyclic tetraamide of any of Examples 10–18 above (525 mg, 1.1 mmol) is dissolved in tetrahydrofuran (40 mL, Aldrich) under N$_2$. Using schlenk techniques, tert-butyllithium (2.6 mL, 4.4 mmol, 1.7 M in 2,4-dimethylpentane, Aldrich) was added to the solution under N$_2$ at −108° C. Ferrous chloride (anhydrous, 155 mg, 1.2 mmol, Alfa) was then added and the solution warmed to room temperature with stirring (16 h), to yield an olive-green precipitate, an air sensitive Fe$^{II}$ complex. Air was admitted through a drying tube (2 h), and the orange solid was collected and washed with CH$_2$Cl$_2$ (2×10 mL). The resulting orange powder was dried under reduced pressure. Yield: 595 mg (>>93%). Because of variable solvation and limited solubility, the lithium salt was converted to the tetraethylammonium salt for further use. The lithium salt (595 mg) in CH$_3$OH (50 mL) was loaded on an ion exchange column (Dowex® 50X2-100, 25 g, 2 cm×12.5 cm) that had been presaturated with [Et$_4$N]$^+$ cations, and the orange band was eluted with CH$_3$OH (100 mL). The solvent was removed under reduced pressure. The residue was suspended in CH$_2$Cl$_2$ (20 mL) and the mixture was filtered. The solvent was removed from the mother liquor under reduced pressure giving an orange hygroscopic glassy residue of [Et$_4$N]2 that was used without further purification. IR (Nujol/NaCl, cm$^{-1}$): 1619 (ν(CO)amide), 1575 (ν(CO) amide), 1534 (ν(CO)amide). Careful purification of an iron (III) starting material was more conveniently approached by dealing with the axial aqua monoanionic complex rather than this axial chloro dianionic complex. [Et$_4$N]2 (550 mg, ca. 0.7 mmol) was dissolved in CH$_3$CN (50 mL). Silver tetrafluoroborate (140 mg. 0.7 mmol) was dissolved in CH$_3$CN (2 mL) and was added to the solution which was stirred (1 h). The AgCl precipitate was filtered off and the solvent removed under reduced pressure. The resulting [Et$_4$N]3 was further purified by elution through a silica gel column (8% MeOH in CH$_3$Cl$_2$). The solvent was removed under reduced pressure and the product was recrystallized from H$_2$O. Yield: 360 mg (>>77% variable solvation with water was found in different microcrystalline samples). IR (Nujo/NaCl, cm$^{-1}$): 1590 (ν(CO)amide), 1565 (ν(CO) amide), 1535 (n(CO) amide). Anal. Calcd for C$_{29}$H$_{46}$N$_5$FeO$_5$Cl$_2$.(H$_2$O): C, 50.52; H, 7.02; N, 10.16: Cl, 10.28. Found: C, 50.24; H, 6.84; N, 9.82; Cl, 10.32. ESIMS (negative ion): m/z 522.2, [3-H$_2$O]$^{1-}$ (100%); m/z 269.7, [3-H$^+$]$^{2-}$ (18%).

EXAMPLE 20

[Et$_4$N]4, [the tetraethylammonium salt of iron(IV) chloro TMDE-DCB monoanion]

[Et$_4$N]2 (500 mg, ca. 0.6 mmol) was dissolved in CH$_2$Cl$_2$ (30 mL). Ammonium cerium(IV) nitrate (10.3 g, 18.3 mmol) was added to the solution and the mixture was stirred (2 h). The solid cerium salts were removed by filtration. The purple product was obtained by removing the solvent under reduced pressure and drying under vacuum. Yield: 400 mg (>>95%). Purple crystals were obtained by recrystallization from CH$_2$Cl$_2$/Et$_2$O. IR (Nujol/NaCl, cm$^{-1}$): 1688 (ν(CO) amide), 1611 (ν(CO) amide), 1582 (ν(CO) amide). ESIMS (negative ion): m/z 557 [4]$^{-1}$ (100%); m/z 522, [4-Cl]$^{1-}$ (65%).

EXAMPLE 21

Synthesis of [Ph$_4$P]5 [the tetraphenylphosphonium salt of iron(IV) cyano TMDE-DCB monoanion] from [Et$_4$N]4 [the tetraethylammonium salt of iron (IV) chloro TMDE-DCB monoanion] and NaCN.

[Et$_4$N]4 [the tetraethylammonium salt of iron(IV) chloro TMDE-DCB monoanion] (225 mg, 0.33 mmol) was suspended in H$_2$O (10 mL). Sodium cyanide (140 mg, 2.85 mmol) was dissolved in H$_2$O (10 mL) and added to the suspension and the mixture was sonicated (Branson 1200, 0.5 h). The purple suspension changed to a deep blue solution and nearly all the solid material dissolved. The mixture was filtered and the blue product was precipitated by adding PPh$_4$Cl [tetraphenylphosphonium chloride] dissolved in water (600 mg, 1.6 mmol, 10 mL, Aldrich). The blue precipitate was collected and washed with H$_2$O (2×10 mL). Yield: 250 mg (0.28 mmole, >>85%). This material (120 mg) was further purified by thin layer chromatography (TLC) (Silica gel plate, GF, 20 cm×20 cm×1000 mm, 10:1 CH$_2$Cl$_2$:CH$_3$CN). The blue material was extracted from the silica gel with CH$_3$CN:CH$_2$Cl$_2$ (1:1, 60 mL). The solvent was removed under reduced pressure and the residue was dissolved in CH$_2$Cl$_2$(3 mL) and filtered. Addition of pentane (150 mL) gave a blue powder (90 mg, 0.10 mmol) Yield on purification: (75%). IR (Nujol/NaCl, cm$^{-1}$): 2129 (ν(CN)), 1659 (ν(CO) amide), 1598 (ν(CO) amide), 1571 (ν(CO) amide). Anal. Calcd for: C$_{46}$H$_{44}$N$_5$FeOCl$_2$P: C, 62.18; H, 4.99; N, 7.88; Cl, 7.98. Found: C, 61.96; H, 5.04; N, 7.84; Cl, 8.06. ESIMS (negative ion): m/z 548.2, [5]$^{1-}$ (100%); m/z 522.1, [5-CN]$^{1-}$ (20%). For $^{13}$C-labeled cyanide: m/z 549.2, [5]$^{1-}$ (100%); m/z 522.1, [5-$^{13}$CN]$^{1-}$ (8%).

EXAMPLE 22

The Synthesis of [Ph$_4$P]5 [the tetraphenylphosphonium salt of iron(IV) cyano TMDE-DCB monoanion] from Nitrile Cyanide Sources.

[Ph$_4$P]5 [the tetraphenylphosphonium salt of iron(IV) cyano TMDE-DCB monoanion] can be formed in the presence or absence of base. In the absence of base, the blue color fades to yellow-orange as the solvent is removed in the workup procedures. Therefore, product isolation to obtain the blue solid is best carried out in the presence of added base at a pH range of 9–10. The following reaction yields [Ph$_4$P]5 with each of CH$_3$CN, CD$_3$CN, CH$_3$CH$_2$CN and (CH$_3$)$_2$CHCN as the solvent substrates. Base was not added to the catalytic reactions described. It was determined that the blue compound is an effective catalyst precursor by adding isolated [Ph$_4$P]5 to an acetonitrile solution of TBHP (tertiary butyl hydroperoxide), both the solvent and oxidant were consumed indicating that although [Ph4P]5 is formed as an end product of the catalytic oxidation process it is not a deactivated form of the catalyst.

EXAMPLE 23

The Synthesis of [Ph$_4$P]5 in the Presence of Base

[Et$_4$N]3 (160 mg, 0.23 mmol) was dissolved in the chosen nitrile solvent (6 mnL), see Example 19. Tetraethylammonium hydroxide base was added (20 wt %, 0.370 mL, 0.52 mmol, Aldrich), then t-butyl hydroperoxide (90%, 0.605 mL, 5.4 mmol, Aldrich) was added dropwise with stirring (20 min) resulting in a blue solution. The remaining nitrile was removed under reduced pressure, leaving an oily blue residue which was dissolved in H$_2$O (15 mL) and filtered. The blue material was precipitated from the filtrate by addition of an aqueous solution of PPh$_4$Cl (800 mg, 2.1 mmol, Aldrich, 10 mL). The blue precipitate was collected and washed with H$_2$O (2×10 mL). Yield: 130, 0.15 mmol (65%). Further purification was carried out as described in the [Ph$_4$P]5 section, Example 25.

EXAMPLE 24

X-ray Crystal Structure Data and Refinement for [Et$_4$N]3 H$_2$O

C$_{29}$H$_{48}$Cl$_2$FeN$_5$O$_6$, M=689.47, Triclinic, Space group P-1, a=9.899(2); b=11.771(2); c=14.991(4)Å, =95.33(2); _=100.09(2); g=92.31(2)°, V=1709.6(6) Å$^3$, D$_{obs}$=1.33 g cm$^{-3}$, D$_{calcd}$(Z=2)=1.339 g cm$^{-3}$, T=293 K, l=0.71069 Å, m=0.64 mm$^{-1}$, trans coeff. 0.87–1.00. Diffraction data were collected at room temperature on an Enraff-Nonius CAD-4 diffractometer using graphite monochromated Mo-Ka radiation. Three reflections were monitored throughout data collection, only random fluctuations in intensity being observed. The structure was solved by direct methods. Hydrogen atoms bonded to the carbon were included in calculated positions with C/H bond distance of 0.96 Å and were refined using a riding model with a thermal parameter 20% greater than the parent carbon. Hydrogen atoms of the water molecule were located from electron density difference maps and their coordinates allowed to refine with the thermal parameter fixed at 20% greater than that of the oxygen. Refinement was by full-matrix least squares on F$^2$ with scattering factors taken from the International Tables. All non-hydrogen atoms were refined with anisotropic thermal parameters. The final difference maps were featureless. Refinement converged to R=0.053, wR2=0.112 with weights 1.0/[s$^2$F$_o^2$)+{0.0652 (F$_o^2$+2F$_c^2$)/3}$^2$] for 2262 observed reflections.

EXAMPLE 25

X-ray Crystal Structure Data and Refinement for [Et$_4$N]4

Single crystals of [Et$_4$N]4. at 20±1° C. are monoclinic, space group P2$_1$/c-C$^5_{2h}$ (No. 14) with α=9.958(2) Å, b=14.956(3) Å, c=22.688(5) Å, a=90.00,$_{13}$ =93.83(2), g=90.00, V=3372(1) Å$^3$, and Z=4 (d$_{calcd}$=1.357 g cm$^{-3}$: m$_a$(CuKa)=6.17 mm$^{-1}$). A total of 4626 independent absorption-corrected reflections having 2q(CuKa)<115.0° were collected using Q-2Q scans and Ni-filtered CuKa radiation. The structure was solved using "Direct Methods" techniques with the NICOLET SHELXTL software package as modified at Crystalytics Company. The resulting structural parameters have been confined to a convergence of R$_1$ (unweighted, based on F)=0.037 for 2680 independent reflections having 2Q(CuKa)<115.00° and I>3s(I). The ten methyl groups were refined as rigid motors with sp$^3$-hybridized geometry and a C—H bond length of 0.96 Å. The initial orientation of each methyl group was determined from difference Fourier positions for the hydrogen atoms. The final orientation of each methyl group was determined by three rotational parameters. The refined positions for the rigid rotor methyl groups have C—C—H angles which ranged from 103°–118°. The remaining hydrogen atoms were included in the structure factor calculations as idealized atoms (assuming sp$^2$- or sp$^3$-hybridization of the carbon atoms and a C—H bond length of 0.96 Å) riding on their respective carbon atoms. The isotropic thermal parameter of each hydrogen atom was fixed at 1.2 times the equivalent isotropic thermal parameter of the carbon to which it is covalently bonded.

EXAMPLE 26

Lignin Bleaching With Hydrogen Peroxide and [Fe(H$_2$O)DCB*]$^-$ at pH 10

Into a 1 cm pathlength quartz cuvette containing 3.0 mL of 0.1 M NaHCO$_3$/Na$_2$CO$_3$ (pH 10) thermostatted at 25° C. was added 60 μL of a saturated alkali lignin solution and 300 μL of catalyst stock solution (1.24×10$^{-4}$ M [Fe(H$_2$O)DCB*]$^-$ (wherein R' and R" are methyl as implied by the * and the counter ion is the tetraethyl ammonium cation), all in water. The solution was stirred and 3.8 μL of 30% H$_2$O$_2$ was added. Absorbance changes at 350, 376, 400, 426, 450, and 476 nm were measured using a Hewlett-Packard UV/Vis spectrophotometer operating in the single cell Kinetics mode. Upon addition of the H$_2$O$_2$, the absorbance increased rapidly at all wavelengths and then decreased rapidly. After 15 min the absorbance at each wavelength was below the starting value indicating that lignin bleaching had occurred. A second addition of 60 μL of lignin was added which caused the absorbances to rise rapidly like before and then following the initial rise decrease more slowly than before. Bubbles formed throughout the experiment.

After 30 mins., an additional 3.8 μL of H$_2$O$_2$ was added. The behavior was similar to that observed previously. A rapid increase in absorbance followed by a decay.

EXAMPLE 27

Lignin Bleaching Without [Fe(H$_2$O)DCB*]$^-$ at pH 10

The steps of Example 26 were repeated with the exclusion of the catalyst. Into a 1 cm pathlength quartz cuvette containing 3.0 mL of 0.1 M NaHCO$_3$/Na$_2$CO$_3$ (pH 10) thermostatted at 25° C. was added 60 μL of a saturated alkali lignin solution and the mixture stirred. A short period after data acquisition was initiated, 3.8 μL of 30% H$_2$O$_2$ was added.

The absorbance measurements were taken using the same parameters as in Example 26.

Upon addition of the $H_2O_2$, all six wavelengths showed a rise in absorbance. The rise was not rapid and did not spike as in the catalyzed reaction. The absorbance gradually began to slope downwards, but did so very slowly. No bubbles were observed in the mixture within the first 15 min. By the end of the hour, bubbles began to appear.

Comparison of the preliminary experiments in Examples 26 and 27 indicate that the addition of the activator of the present invention increases the rate at which $H_2O_2$ bleaches lignin.

EXAMPLE 28

Lignin Bleaching With Hydrogen Peroxide, A Sequesterant and No [Fe($H_2O$)DCB*]⁻ at pH 10

The steps of Example 27 were repeated with the addition of a sequesterant, DEQUEST 2066, 2 $\mu$L, a chelating agent for free metal ions. The addition of $H_2O_2$ gave a gradual rise and decay pattern similar to that seen in Example 27.

EXAMPLE 29

Lignin Bleaching With Hydrogen Peroxide, A Sequesterant and no [Fe($H_2O$)DCB*]⁻ at pH7

The steps of Example 27 were repeated at pH 7 using a 0.0087 molal $KH_2PO_4$/0.030 molal $Na_2HPO_4$ buffer. 2 $\mu$L DEQUEST 2066 chelating agent was added to the cuvette. No discernible bleaching occurred within the 1 hr timeframe of the experiment. Minimal activity was observed in the 350nm absorbance trace, but was attributed to noise.

EXAMPLE 30

Lignin Bleaching With Hydrogen Peroxide, [Fe($H_2O$) DCB*]⁻ and a Sequesterant at pH 10

Into a cuvette equipped with a stir bar, 1 equivalent of the catalyst of Example 26 (300 $\mu$L stock solution of [Fe($H_2O$) DCB*]⁻), 60 $\mu$L saturated lignin solution buffered as before and 2 $\mu$L DEQUEST chelating agent were mixed. Absorbance was measured using the same parameters as described in Examples 26 and 27.

After 1–2 min., 1000 equivalents 30% $H_2O_2$ (3.8 $\mu$L) was added to the cuvette. This caused the rapid rise in absorbance followed by rapid decrease as described in Example 26.

After 20 min., an additional 60 $\mu$L lignin was added to the cuvette. The absorbance at all wavelengths rose more slowly and then decayed more slowly than following the addition of the $H_2O_2$.

After 30 min., an additional equivalent (300 $\mu$L) of catalyst ([Fe($H_2O$)DCB*]⁻) was added. No significant changes were observed.

After 40 min., an additional 3.8 $\mu$L $H_2O_2$ was added to the cuvette. This caused a significant decrease in the absorbance at all wavelengths indicating that lignin bleaching was again occurring.

EXAMPLE 31

Lignin Bleaching With Hydrogen Peroxide, [Fe($H_2O$)DCB*]⁻, and A Sequesterant at pH 7.

Example 29 was repeated but with the addition of 300 $\mu$L catalyst. 3.8 $\mu$L 30% $H_2O_2$ was added after a few cycles. Upon the addition of $H_2O_2$, the absorbances rose at each of the six wavelengths used in Example 26, but not dramatically. The absorbances continued to rise slowly for the first 15 min., plateaued, and then began to fall for all six wavelengths. After one hour, the absorbances were higher than the initial absorbance.

EXAMPLE 32

Sustained Catalyst Activity

Into a 1 cm pathlength quartz cuvette containing 3.0 mL if 0.1 M $NaHCO_3$/$Na_2CO_3$ (pH 10) thermostatted at 25° C. was added 60 $\mu$L of a saturated alkali lignin solution, 300 $\mu$L (12.4 $\mu$M) of catalyst stock solution (1.24×10⁻⁴M [Fe($H_2O$) DCB*]⁻), and 2 $\mu$L Dequest 2066 all in water. The mixture was stirred, data acquisition was initiated as in Example 26, and then 19 $\mu$L (5000 equivalents) of 30% $H_2O_2$ was added. After the first rapid rise in absorbance followed by rapid decay, aliquots of 60 $\mu$L saturated alkali lignin solution and 19 $\mu$L (5000 equivalents) of 30% $H_2O_2$ were added every 15 min.

Figure 1:
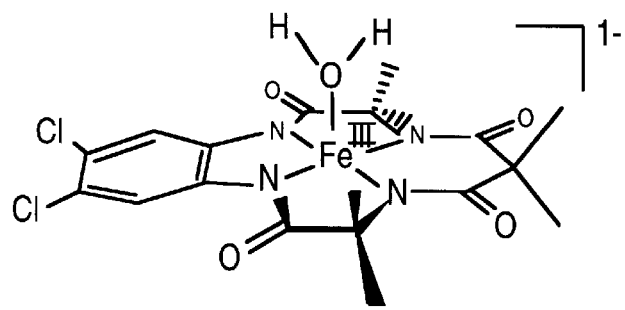
FIG. 1 is a graph showing the sustained activating stability of the preferred compound of the present invention when added with hydrogen peroxide to a sample of lignin as compared to a control using hydrogen peroxide alone.
Figure 1:
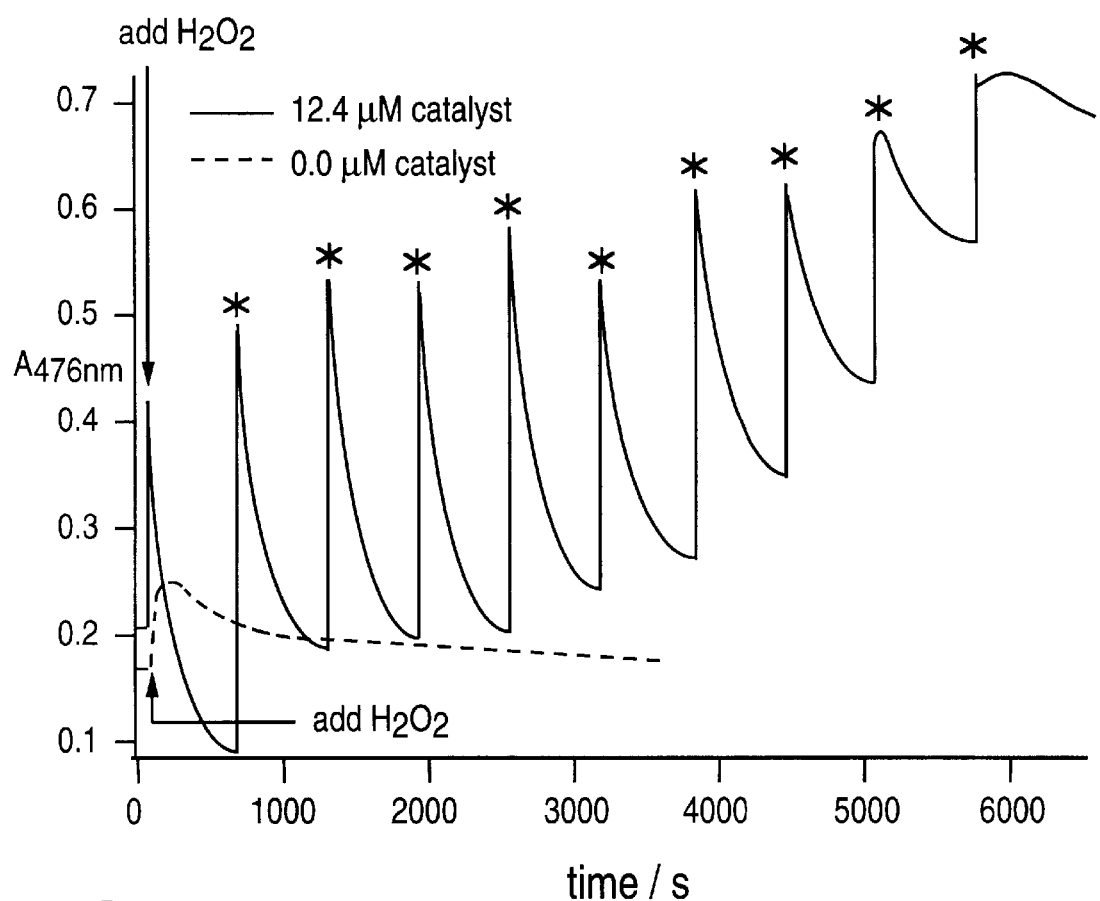
Figure 2:
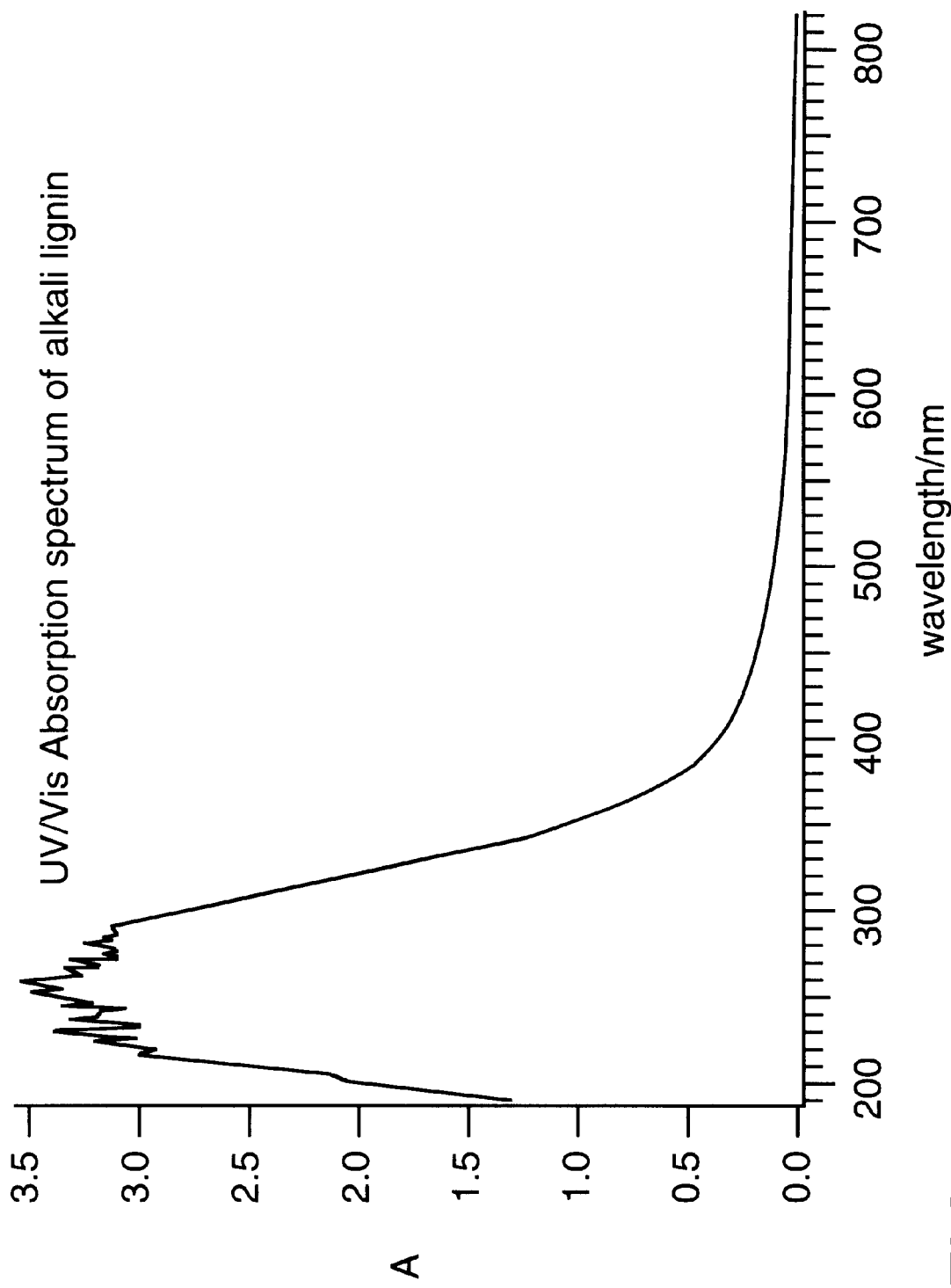
FIG. 2 represents the UV/Visual absorption spectrum of alkali lignin.

The results obtained at the 476 nm monitored wavelength are shown by the solid line in the graph of FIG. 1. Similar results were obtained at the other wavelengths monitored. Additions of lignin and $H_2O_2$ are shown by asterisks.

For comparison, a cuvette of the saturated solution of lignin, chelating agent and $H_2O_2$ without catalyst was prepared and the absorbance measured. The results are shown by the dashed line in FIG. 1.

EXAMPLE 33

Sustained Catalyst Stability

Figure 5:
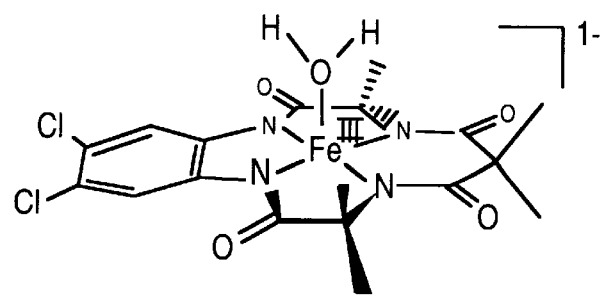
FIG. 5 is a graph comparing the sustained catalyst stabilities of preferred embodiments of the invention versus control.
Figure 5:
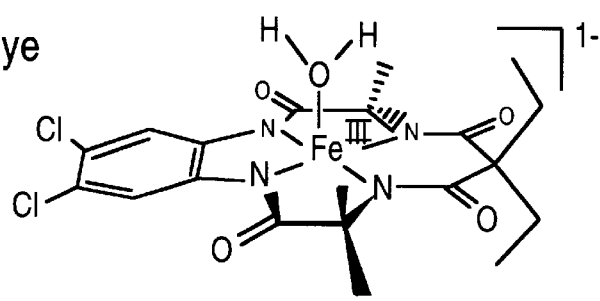
Figure 5:
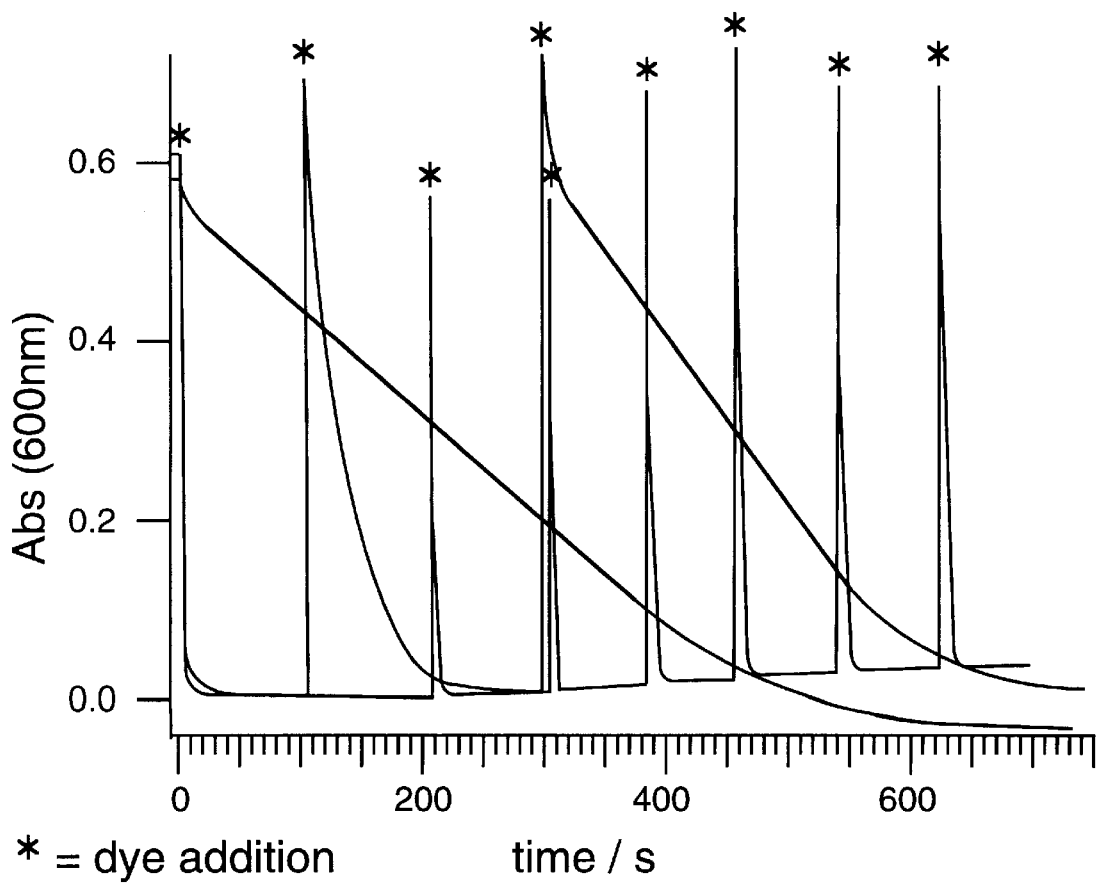

With reference to FIG. 5, the catalytic longevity of two embodiments of the invention were compared in a dye test. Compound 1 had substitutents R' and R" each as $CH_3$, while Compound 2 had substitutes R' and R" each as —$CH_2CH_3$. The control was no catalyst added.

The conditions were pH 9, room temperature (21.1° C.), with a buffer system of $NaHCO_3$/$Na_2CO_3$. Oxidant was 4 mM (30%) $H_2O_2$. At each of the asterisks, 12 $\mu$M pinacyanol chloride dye was added.

As can be seen from the graph in FIG. 5, each addition of dye where Compound 1 was present resulted in almost immediate decolorization. Compound 2, the diethyl compound, had more gradual decolorization. The control showed only a very gradual rate of decolorization.

EXAMPLE 34

Oxidation of 2,4,6-trichlorophenol (TCP)

Figure 6:
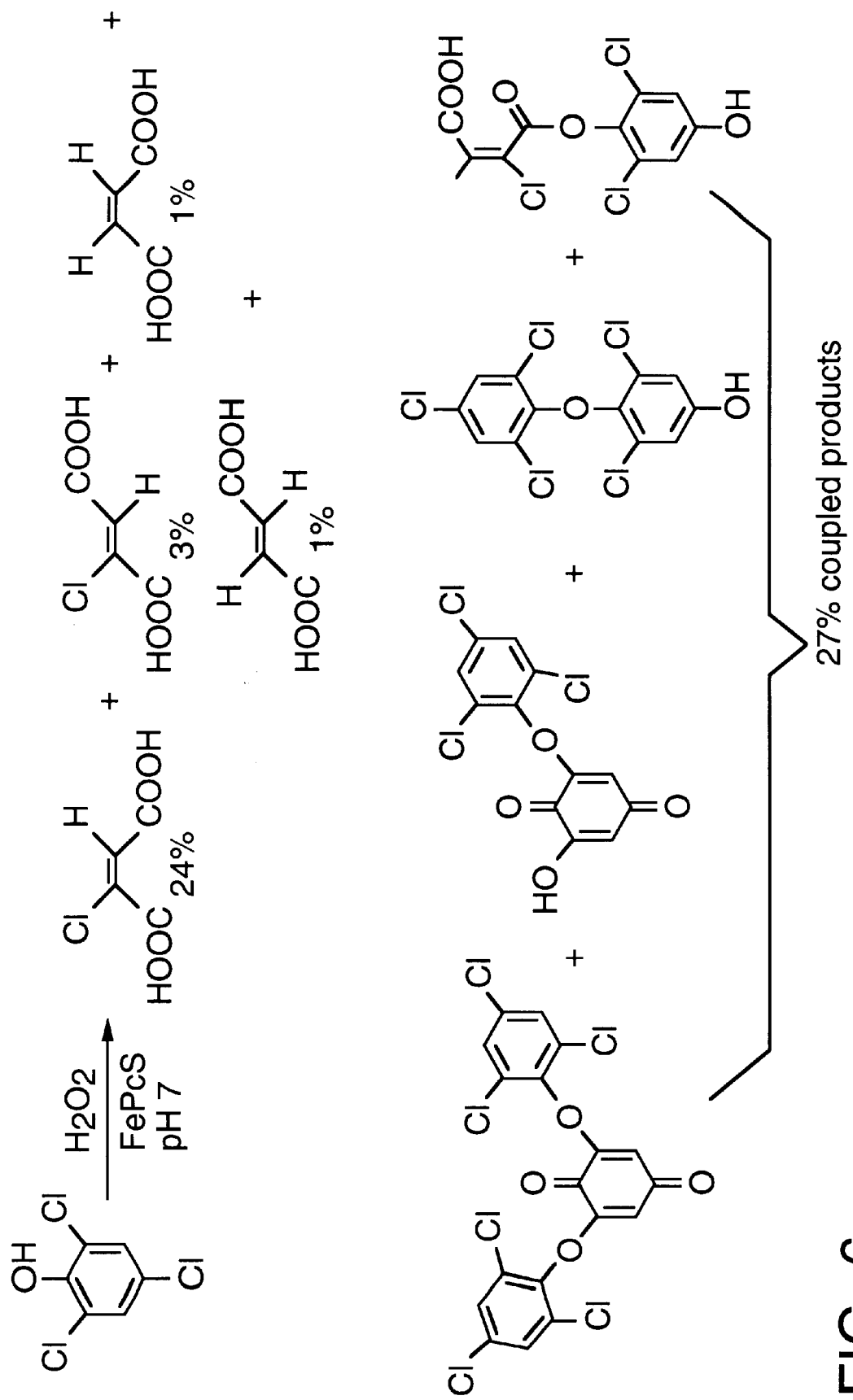
FIG. 6 is shows the products identified from the oxidation of TCP with FePcS and $H_2O_2$ at pH 7.

TCP can be rapidly oxidized under a variety of reaction conditions in water by $H_2O_2$ using the iron complex [Fe($H_2O$)DCB *]⁻, shown in FIG. 1, as the $H_2O_2$ activator. Recent work on TCP oxidation has been performed using either $H_2O_2$ or $KHSO_5$ as the oxidant and the water soluble iron complex of 2,9,16,23-tetrasulfophthalocyanine (FePcS) as the oxidant activator. See, Sorokin, A.; Seris, J.-L.; Meunier, B., Science, vol. 268, pp. 1163–1166 (1995). In those studies, it was found that the TCP was more efficiently degraded to the species shown in FIG. 6 when $KHSO_5$ was the oxidant. However, it is desirable from a practical point of view to use $H_2O_2$ as the oxidant because of its ready availability at low cost. It was reported in the Sorokin et al., Science article referenced above that the compounds labeled "coupled products" in FIG. 6 yield a purple solution. These coupled products are not further oxidized by the FePcS/ $H_2O_2$ system. See, Sorokin, A.; De Suzzoni-Dezard, S.; Poullain, D.; Noel, J.-P.; Meunier, B. J. Am. Chem. Soc., vol.

118, pp.7410–7411 (1996). Since the coupled products are also polychlorinated aromatic compounds, it is likely that they are environmentally undesirable. Evidence is provided herein that [Fe(H$_2$O)DCB*]⁻ further oxidizes some or all of the coupled products of TCP oxidation.

Figure 7:
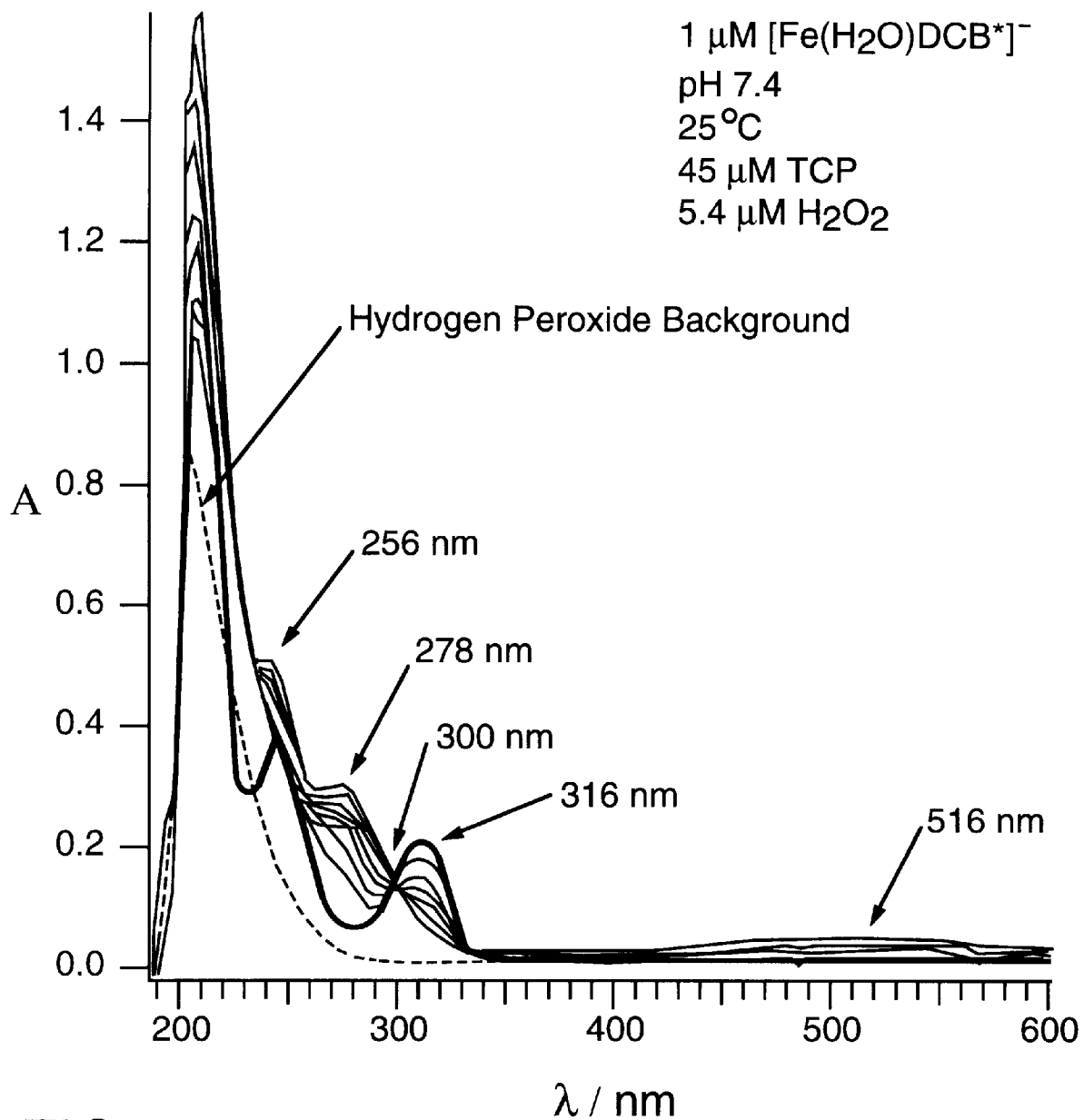
FIG. 7 is a graph showing the changes that occur to the UV/Vis spectrum of TCP following the addition of $H_2O_2$. The bold line is the spectrum of unreacted TCP and the dashed line is that of $H_2O_2$.

In FIG. 7, the changes in the ultraviolet/visible (UV/vis) spectrum that occur when TCP is oxidized in pH 7.4 phosphate buffer by 1 μM [Fe(H$_2$O)DCB*]⁻ in the presence of 5.4 mM H$_2$O$_2$ are shown. In this experiment, [Fe(H$_2$O)DCB*]⁻ and TCP are combined in the pH 7.4 buffer, H$_2$O$_2$ is added, and then the spectral changes monitored. TCP absorbance maxima occur at 220, 256, and 316 nm. The wavelengths selected for kinetic analysis of the oxidation process are indicated in FIG. 7. The results of the analysis are shown on FIG. 8 (for purposes of clarity only the absorption changes for three wavelengths are shown). In the absence of [Fe(H$_2$O)DCB*]⁻ there are no decreases in the absorbance values for bands arising from TCP.

Figure 8:
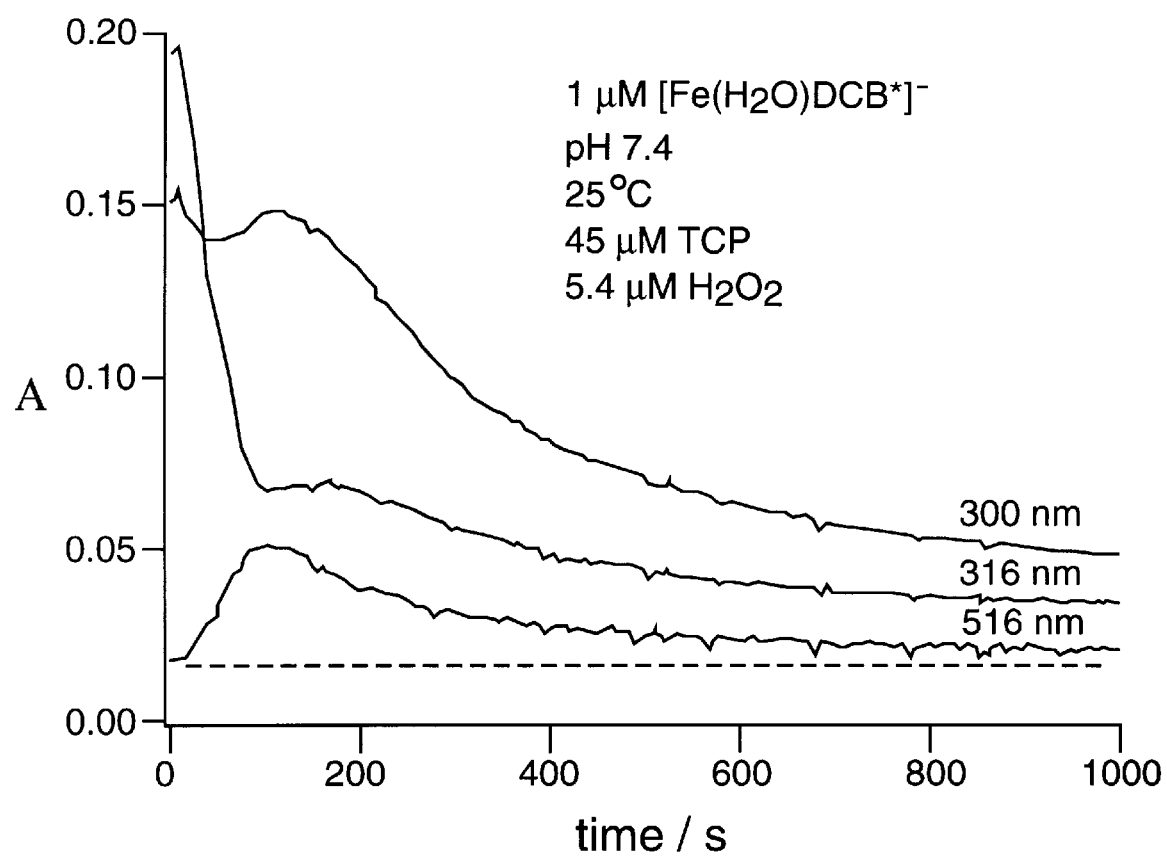
FIG. 8 is a graph showing the absorbance changes at three of the wavelengths indicated in FIG. 7. The * indicates the addition of $H_2O_2$.

It is apparent from FIG. 8 that as the absorbance for the band at 316 nm decreases, a new absorption appears at 516 nm which increases in intensity for approximately 100 s, but then it decreases back to its starting value. In experiments where the reaction was monitored visually, rapid formation of a purple solution occurred after the H$_2$O$_2$ was added and then this solution was gradually bleached ultimately yielding a colorless solution. The purple color is attributed to coupling products like those in FIG. 6. The fact that the solution becomes colorless indicates the [Fe(H$_2$O)DCB*]⁻/H$_2$O$_2$ system is capable of oxidizing these coupled products.

Figure 9:
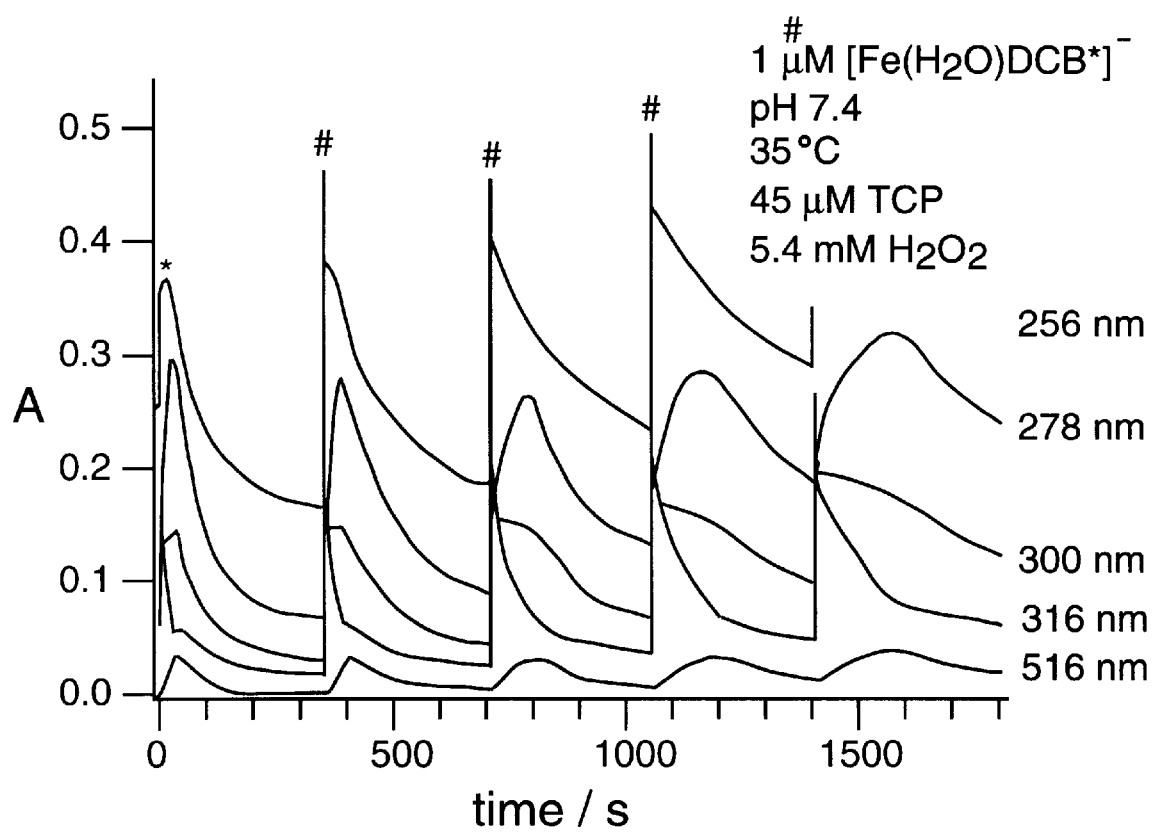
FIG. 9 is a graph showing multiple TCP oxidations using the $[Fe(H_2O)DCB^*]^-/H_2O_2$ system under the conditions shown on the figure. An $H_2O_2$ addition is indicated by * and a TCP addition is indicated by #.

The [Fe(H$_2$O)DCB*]⁻/H$_2$O$_2$ system is capable of performing multiple oxidations of TCP, as shown in FIG. 9. The experimental procedures were the same as those used in FIG. 8 (note, however, the higher temperature for FIG. 9) but following the first oxidation cycle of TCP additional 45 μM portions of TCP were added, marked with a #, when the absorbance at 516 nm had returned essentially to its starting value. The first portion of TCP is oxidized within 100 s while the fifth portion added, marked with a #, when the absorbance at 516 nm had returned essentially to its starting value. The first portion of TCP is oxidized within 100 s while the fifth portion requires greater than 400 s to be oxidized. The slowing down of the oxidation process probably arises from a combination of [Fe(H$_2$O)DCB*]⁻ decomposition and further oxidation of some of the TCP oxidation products by [Fe(H$_2$O)DCB*]⁻.

Figure 10A:
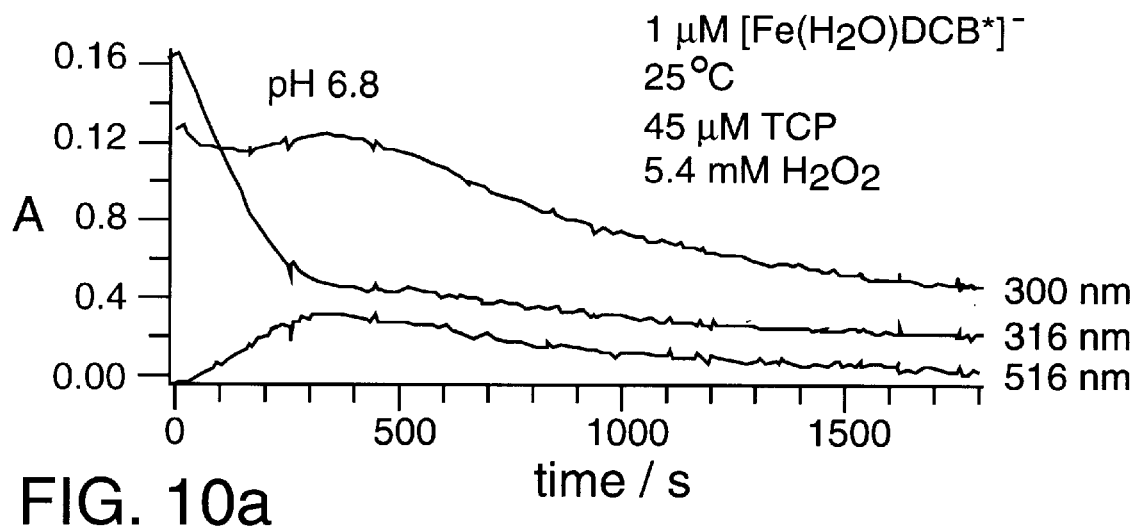
FIG. 10 is a series of three graphs showing oxidation of TCP at pH 6.8, pH 7.4 and pH 10 using the $[Fe(H_2O)DCB^*]^-/H_2O_2$ system. All operating conditions are identical in the three cases except for pH.
Figure 10B:
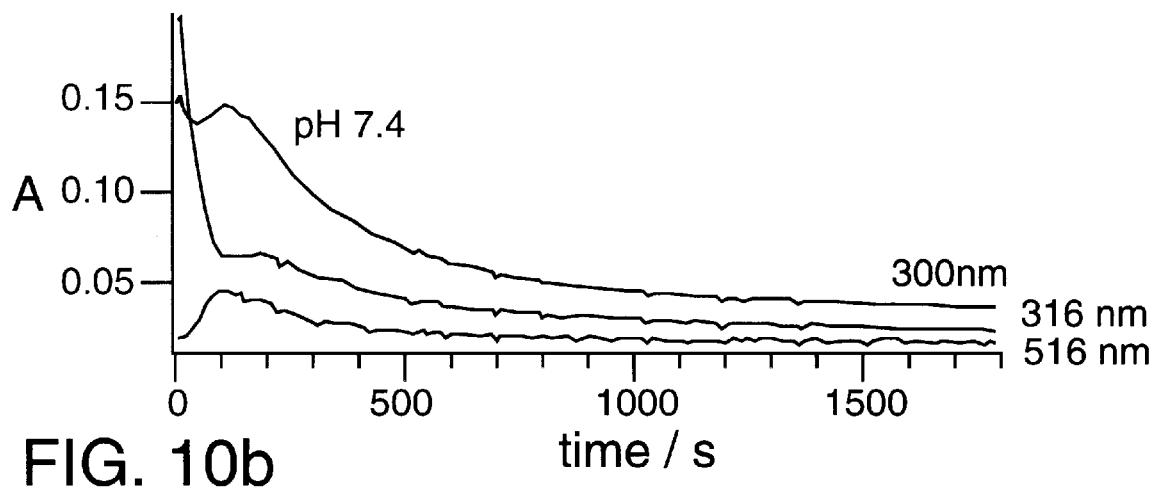
Figure 10C:
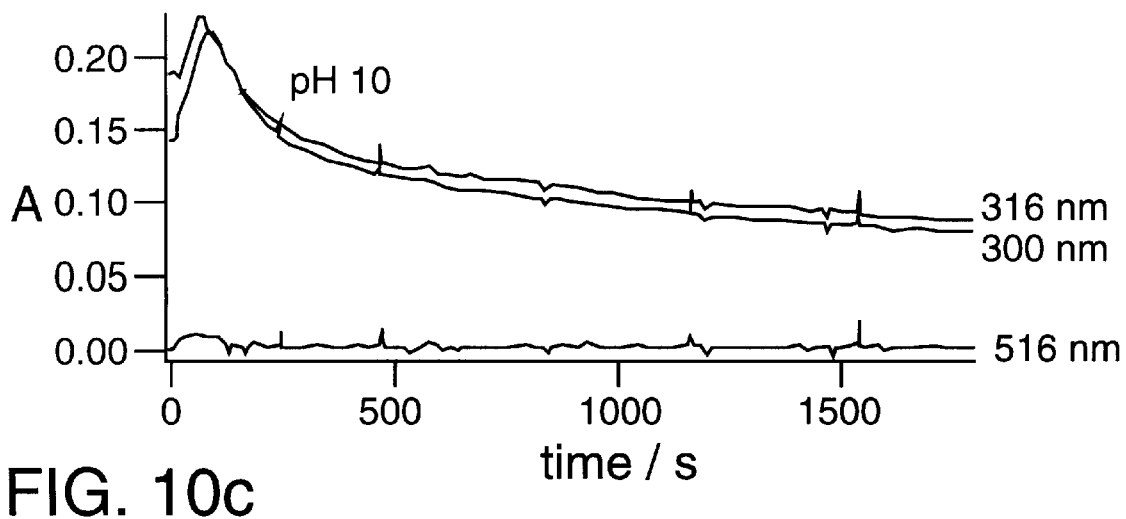

The [Fe(H$_2$O)DCB*]⁻/H$_2$O$_2$ system oxidizes TCP at a variety of pH's. Shown in FIG. 10 are kinetic traces for the oxidation of TCP under the conditions indicated on the figure. The data indicate that TCP oxidation is most rapid at pH 10. However, unlike the results shown in FIG. 9, multiple TCP oxidation cycles are not achievable using a single charge of [Fe(H$_2$O)DCB*]⁻. Also the absorption changes at 300 and 316 nm are more complicated at pH 10 indicating enhanced complexity for the oxidation process. Thus, of the three pH values tested in this experiment, the optimal value under the conditions of the experiment with respect to time and activator longevity appear to be those at pH 7.4. This is a very significant result because effluent discharge to lakes and streams should take place in the pH 7 range.

EXPERIMENT 35

Effluent Decolorization

Two 25 mL samples of effluent having a strong, dirty black/brown color obtained from a pulp and paper processing mill in Tasman, New Zealand, were prepared in pH 11 solution. To one of these solutions was added 25 mg H$_2$O$_2$ and 12.5 μg of the [Fe(H$_2$O)DCB*]⁻ activator. After four hours the absorbance value of the sample at 465 nm was measured using a visible spectrophotometer. The additives are shown in the table below.

| Sample | Absorbence at 465 nm | H$_2$O$_2$ consumed, mg |
|---|---|---|
| 1. Effluent + water | 0.153 | — |
| 2. Effluent + H$_2$O$_2$ | 0.058 | 9.2 |
| 3. Effluent + H$_2$O$_2$ + Activator | 0.025 | 13.5 |

The sample containing the activator was a faint yellow color after treatment. Visual inspection of the solution that contained the activator indicated that the reduction of the back/brown solution to pale yellow was actually completed within the first hour of treatment, at about 30–60 minutes. Comparable changes were not observed for the H$_2$O$_2$ solution alone.

What is claimed is:

1. A bleaching composition comprising:
    (a) an oxidatively stable activator having the structure

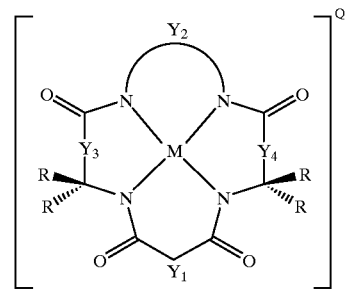

wherein Y$_1$, Y$_3$ and Y$_4$ each represents a bridging group having zero, one, two or three carbon containing nodes for substitution, and Y$_2$ is a bridging group having at least one carbon containing node for substitution, each said node containing a C(R), [C(R$_1$)(R$_2$),] or a C(R)$_2$ unit and each R substituent is the same or different from the remaining R substituents and (i) is selected from the group consisting of methyl, cycloalkyl, cycloalkenyl, alkenyl, aryl, alkynyl, alkylaryl, halogen, alkoxy, phenoxy, CH$_2$CF$_3$, CF$_3$ and combinations thereof, or (ii) form a substituted or unsubstituted benzene ring of which two carbon atoms in the ring form nodes in the Y unit, or (iii) together with a paired R substituent bound to the same carbon atom form a cycloalkyl or cycloalkenyl ring, which may include an atom other than carbon; M is a transition metal with oxidation states of I, II, III, IV, V, VI, VII or VIII or selected from Groups 3, 4, 5, 6, 7, 8, 9, 10, 11 and 12 of the Periodic Table ofthe Elements; and Q is any counterion which would balance the charge of the compound on a stoichiometric basis; and
    (b) an amount of a source of an oxidant effective for oxidizing byproducts of the pulp and paper making process.

2. The composition of claim 1 further comprising a further adjunct selected from the group consisting of sequesterants and cellulose-based material bleaching adjuncts.

3. A The composition of claim 1 further comprising a ligand L bound to the metal M.

4. The composition of claim 1 wherein the oxidant is a peroxy compound or ozone.

5. The composition of claim 4 wherein said peroxy compound is selected from the group consisting of hydrogen peroxide, hydrogen peroxide adducts, compounds capable of producing hydrogen peroxide in aqueous solution, organic peroxides, persulfates, perphosphates, and persilicates.

6. The composition of claim 1 wherein the oxidatively stable activator is a macrocyclic tetraamido metal-ligand complex having the structure:

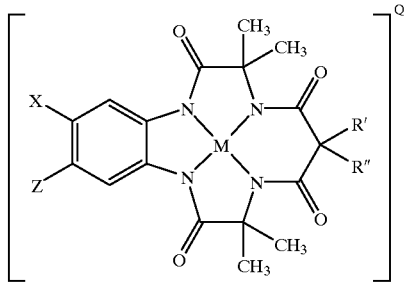

wherein X and Z may be H, electron donating or electron-withdrawing groups and R' and R" may be any combination of H, alkyl, cycloalkyl, cycloalkenyl, alkenyl, aryl, alkynyl, alkylaryl, halogen, alkoxy, or phenoxy substituents, or combine to form a cycyloalkyl or cycloalkenyl ring, which may contain at least one atom that is not carbon.

7. The composition of claim 6 wherein X and Z are independently selected from the group consisting of H, halogen, $SO_3$, $OSO_3$, $OSO_3R$ (wherein R is H, alkyl, aryl, or alkylaryl) and $NO_2$.

8. The composition of claim 6 wherein R' and R" are selected from H and $C_{1-6}$ alkyl.

9. The composition of claim 6 wherein M is Fe or Mn.

10. The composition claim 6 wherein R' and R" are selected from H, $CH_3$, $CF_3$, halogen, or join together to form a cycloalkyl or cycloalkenyl, optionally with at least one atom which is not carbon.

11. The composition of claim 6 wherein X and Z are H.

12. A bleaching composition comprising:

(a) an oxidatively stable activator having the structure

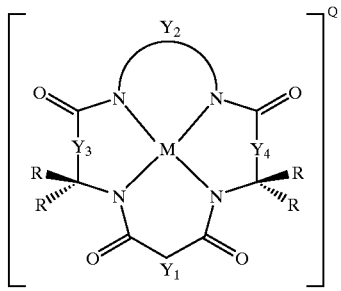

wherein $Y_1$, $Y_3$ and $Y_4$ each represents a bridging group having zero, one, two or three carbon containing nodes for substitution, and $Y_2$ is a bridging group having at least one carbon containing node for substitution, each said node containing a C(R) or a C(R)$_2$ unit and each R substituent is the same or different from the remaining R substituents and (i) is selected from the group consisting of methyl, cycloalkyl, cycloalkenyl, alkenyl, aryl, alkynyl, alkylaryl, halogen, alkoxy, phenoxy, $CH_2CF_3$, $CF_3$ and combinations thereof, or (ii) form a substituted or unsubstituted benzene ring of which two carbon atoms in the ring form nodes in the Y unit, or (iii) together with a paired R substituent bound to the same carbon atom form a cycloalkyl or cycloalkenyl ring, which may include an atom other than carbon; M is a transition metal with oxidation states of I, II, III, IV, V, VI, VII or VIII or selected from Groups 3, 4, 5, 6, 7, 8, 9, 10, 11 and 12 of the Periodic Table of the Elements; and Q is any counterion which would balance the charge of the compound on a stoichiometric basis; and (b) an amount of a source of an oxidant effective for oxidizing products selected from the group consisting of chromophores, absorbable organic nonaromatic halogen species, and high molecular mass material species.

13. A bleaching composition comprising:

(a) an oxidatively stable activator having the structure

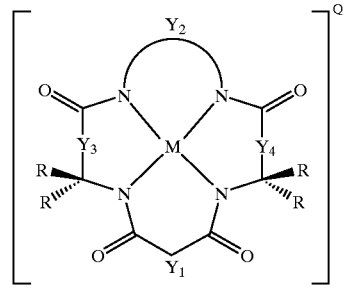

wherein $Y_1$, $Y_3$ and $Y_4$ each represents a bridging group having zero, one, two or three carbon containing nodes for substitution, and $Y_2$ is a bridging group having at least one carbon containing node for substitution, each said node containing a C(R) or a C(R)$_2$ unit and each R substituent is the same or different from the remaining R substituents and (i) is selected from the group consisting of methyl, cycloalkyl, cycloalkenyl, alkenyl, aryl, alkynyl, alkylaryl, halogen, alkoxy, phenoxy, $CH_2CF_3$, $CF_3$ and combinations thereof, or (ii) form a substituted or unsubstituted benzene ring of which two carbon atoms in the ring form nodes in the Y unit, or (iii) together with a paired R substituent bound to the same carbon atom form a cycloalkyl or cycloalkenyl ring, which may include an atom other than carbon; M is a transition metal with oxidation states of I, II, III, IV, V, VI, VII or VIII or selected from Groups 3, 4, 5, 6, 7, 8, 9, 10, 11 and 12 of the Periodic Table of the Elements; and Q is any counterion which would balance the charge of the compound on a stoichiometric basis; and (b) an amount of a source of an oxidant effective for oxidizing aromatic organic halogen species selected from the group consisting of chlorinated phenols, dioxins, dibenzoflurans, biphenyls and combinations thereof, or chlorinated lignin degradation products.

* * * * *

UNITED STATES PATENT AND TRADEMARK OFFICE
CERTIFICATE OF CORRECTION

PATENT NO.   : 6,136,223
DATED        : October 24, 2000
INVENTOR(S)  : Collins et al.

It is certified that error appears in the above-identified patent and that said Letters Patent is hereby corrected as shown below:

DRAWINGS,
In the figure at the bottom, delete "0.4mM [Fe(H$_2$O)DCB*]$^-$" and substitute therefor -- 0.4 μm [Fe(H$_2$O)DCB*]$^-$ --;
Delete "0.4mM [Fe(H$_2$O)DCB]$^-$" and substitute therefor -- 0.4 μM [Fe(H$_2$O)DCB]$^-$ --;
After "0.0" delete "mM";

Figure 5, delete "0.4mM [FeH$_2$O)DCB*]$^-$" and substitute therefor
-- 0.4 μM [Fe(H$_2$O)DCB*]$^-$ --;
Delete "0.4mM [Fe(H$_2$O)DCB]$^-$" and substitute therefor -- 0.4 μM [FeH$_2$O)DCB]$^-$ --;
Figure 5, after "0.0" delete "mM";
Figure 7, delete "5.4 μM H$_2$O$_2$" and substitute therefor -- 5.4 mN H$_2$O$_2$ --;
Figure 8, delete "5.4 μM H$_2$O$_2$" and substitute therefor -- 5.4 mM H$_2$O$_2$ --;

ABSTRACT,
Line 19, (excluding the drawing), delete "10 and 11" and substitute therefor -- 10, 11 and 12 --;

Column 3,
Line 7, delete "is" and substitute therefor -- it --;
Line 21, delete "morl" and substitute therefor -- mol --;

Column 4,
Line 26, delete "material-can" and substitute therefor -- material can --;

Column 8,
Line 11, delete "is";

Column 11,
Line 28, delete "ax" and substitute therefor -- α --;
Line 48, delete "works" and substitute therefor -- work --;

Column 15,
Line 54, delete "include" and substitute therefor -- included --;
Line 60, delete "enzymes" and substitute therefor -- enzymes' --;

UNITED STATES PATENT AND TRADEMARK OFFICE
CERTIFICATE OF CORRECTION

PATENT NO. : 6,136,223
DATED : October 24, 2000
INVENTOR(S) : Collins et al.

It is certified that error appears in the above-identified patent and that said Letters Patent is hereby corrected as shown below:

Column 16,
Line 36, delete "nitrites" and substitute therefor -- nitriles --;

Column 17,
Line 48, before "introduced" insert -- were --;

Column 18,
Line 52, delete "39" and substitute therefor -- 35 --;

Column 21,
Line 17, delete "[cm $^{31\ 1}$]" and substitute therefor -- [cm$^{-1}$] --;

Column 22,
Line 57, insert -- . -- between "$CH_{21}H_{10}N_4O_4$" and "$H_2O$";

Column 23,
Line 6, delete "nujo" and substitute therefor -- nujol --;
Line 27, delete "nujo" and substitute therefor -- nujol --;
Line 30, insert ";" after "58.90";

Column 25,
Line 12, delete "$^3C$" and substitute therefor -- $^{13}C$ --;
Line 28, delete "[Fe ($H_2O$) DCB]$^{31}$" and substitute therefor -- [Fe ($H_2O$) DCB]$^-$ --;

Column 26,
Line 1, delete "Nujo" and substitute therefor -- Nujol --;

Column 27,
Line 10, delete "[Ph4P]5" and substitute therefor -- [Ph$_4$P]5 --;
Line 18, delete "mnL" and substitute therefor -- mL --;

Column 28,
Line 1, delete "$_{13}$" and substitute therefor -- _ --;

Column 30,
Line 34, delete "substitutes" and substitute therefor -- substituents --;

UNITED STATES PATENT AND TRADEMARK OFFICE
CERTIFICATE OF CORRECTION

PATENT NO.   : 6,136,223
DATED        : October 24, 2000
INVENTOR(S)  : Collins et al.

It is certified that error appears in the above-identified patent and that said Letters Patent is hereby corrected as shown below:

Column 31,
Line 63, delete "EXPERIMENT" and substitute therefor -- EXAMPLE --;

Column 32,
Line 19, delete "back" and substitute therefor -- black --;
Line 43, delete "[C($R_1$)($R_2$),]";
Line 57, delete "ofthe" and substitute therefor -- of the --; and Column 34,
Line 62, delete "dibenzoflurans" and substitute therefor -- dibenzofurans --.

Signed and Sealed this

Twenty-seventh day of November, 2001

Attest:

NICHOLAS P. GODICI
Attesting Officer    Acting Director of the United States Patent and Trademark Office

UNITED STATES PATENT AND TRADEMARK OFFICE
CERTIFICATE OF CORRECTION

PATENT NO. : 6,136,223
DATED : October 24, 2000
INVENTOR(S) : Collins et al.

It is certified that error appears in the above-identified patent and that said Letters Patent is hereby corrected as shown below:

Title page,
ABSTRACT, line 19, (excluding the drawing), delete "10 and 11" and substitute therefor-- 10, 11 and 12 --;

Drawings,
In the figure at the bottom of page 1, delete "0.4 mM [Fe(H$_2$O)DCB*]$^-$" and substitute therefor -- 0.4 µM[Fe(H$_2$O)DCB*]$^-$ --;
In the figure at the bottom of page 1, delete "0.4 mM [Fe(H$_2$O)DCB]$^-$" and substitute therefor -- 0.4 µM[Fe(H$_2$O)DCB]$^-$ --;
In the figure at the bottom of page 1, after "0.0" delete "mM";

Figure 5, delete "0.4 mM [Fe(H$_2$O)DCB*]$^-$" and substitute therefor
--0.4 µM[Fe(H$_2$O)DCB*]$^-$ --;
Figure 5, delete "0.4 mM [Fe(H$_2$O)DCB]$^-$" and substitute therefor
--0.4 µM[Fe(H$_2$O)DCB]$^-$ --;
Figure 5, after "0.0" delete "mM";

Figure 7, delete "5.4 µM H$_2$O$_2$" and substitute therefor -- 5.4 mM H$_2$O$_2$ --;

Figure 8, delete "5.4 µM H$_2$O$_2$" and substitute therefor -- 5.4 mM H$_2$O$_2$ --;

Column 3,
Line 7, delete "is" and substitute therefor -- it --;
Line 21, delete "morl" and substitute therefor -- mol --;

Column 4,
Line 26, delete "material-can" and substitute therefor -- material can --;

Column 8,
Line 11, delete "is";

Column 11,
Line 28, delete "ax" and substitute therefor -- α- --;
Line 48, delete "works" and substitute therefor -- work --;

Column 15,
Line 54, delete "include" and substitute therefor -- included --;
Line 60, delete "enzymes" and substitute therefor -- enzymes' --;

Column 16,
Line 36, delete "nitrites and substitute therefor -- nitriles --;

UNITED STATES PATENT AND TRADEMARK OFFICE
CERTIFICATE OF CORRECTION

PATENT NO. : 6,136,223
DATED : October 24, 2000
INVENTOR(S) : Collins et al.

It is certified that error appears in the above-identified patent and that said Letters Patent is hereby corrected as shown below:

Column 17,
Line 48, before "introduced" insert -- were --;

Column 18,
Line 52, delete "39" and substitute therefor -- 35;

Column 21,
Line 17, delete "[cm $^{31\ 1}$]" and substitute therefor -- cm$^{-1}$] --;

Column 22,
Line 57, insert -- . -- between "$CH_{21}H_{10}N_4O_4$" and "$H_2O$";

Column 23,
Lines 6, and 27, delete "nujo" and substitute therefor -- nujol --;
Line 30, insert ";" after "58.90";

Column 25,
Line 12, delete "$^3C$" and substitute therefor -- $^{13}C$ --;
Line 28, delete "[Fe ($H_2O$) DCB]$^{31}$" and substitute therefor -- [Fe ($H_2O$) DCB]$^-$ --;

Column 26,
Line 1, delete "Nujo" and substitute therefor -- Nujol --;

Column 27,
Line 10, delete "[Ph4P]5" and substitute therefor -- [Ph$_4$P]5 --;
Line 18, delete "mnL" and substitute therefor -- mL --;

Column 28,
Line 1, delete "$_{13}$" and substitute therefor -- _ --;

Column 30,
Line 34, delete "substitutes" and substitutes therefor -- substituents --;

Column 31,
Line 63, delete "EXPERIMENT" and substitute therefor -- EXAMPLE --;

Column 32,
Line 19, delete "back" and substitute therefor -- black --;
Line 43, delete "[C($R_1$)($R_2$),]";
Line 57, delete "ofthe" and substitute therefor -- of the --; and

UNITED STATES PATENT AND TRADEMARK OFFICE
CERTIFICATE OF CORRECTION

PATENT NO.   : 6,136,223
DATED        : October 24, 2000
INVENTOR(S)  : Collins et al.

It is certified that error appears in the above-identified patent and that said Letters Patent is hereby corrected as shown below:

Column 34,
Line 62, delete "dibenzoflurans" and substitute therefor -- dibenzofurans --.

Signed and Sealed this

Fifth Day of February, 2002

Attest:

Attesting Officer

JAMES E. ROGAN
Director of the United States Patent and Trademark Office